(12) United States Patent
Kim et al.

(10) Patent No.: US 12,089,668 B2
(45) Date of Patent: Sep. 17, 2024

(54) MASK APPARATUS AND METHOD FOR CONTROLLING THE SAME

(71) Applicant: LG ELECTRONICS INC., Seoul (KR)

(72) Inventors: Minsoo Kim, Seoul (KR); Jinmoo Park, Seoul (KR); Seonghun Lee, Seoul (KR); Junchan Kwon, Seoul (KR); Sooyong Park, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 191 days.

(21) Appl. No.: 17/846,544

(22) Filed: Jun. 22, 2022

(65) Prior Publication Data

US 2023/0014547 A1 Jan. 19, 2023

(30) Foreign Application Priority Data

Jul. 19, 2021 (KR) .................. 10-2021-0093999

(51) Int. Cl.
*A41D 13/11* (2006.01)
*A41D 1/00* (2018.01)
(Continued)

(52) U.S. Cl.
CPC .............. *A41D 13/11* (2013.01); *A41D 1/002* (2013.01); *H04R 1/025* (2013.01); *H04R 1/08* (2013.01); *H04R 2201/02* (2013.01)

(58) Field of Classification Search
CPC ........ A41D 13/11; A41D 1/002; H04R 1/025; H04R 1/08; H04R 2201/02
(Continued)

(56) References Cited

U.S. PATENT DOCUMENTS 5,159,641 A 10/1992 Sopko et al.
5,307,793 A 5/1994 Sinclair et al.
(Continued)

FOREIGN PATENT DOCUMENTS

CN 103127633 6/2013
CN 104540539 4/2015
(Continued)

OTHER PUBLICATIONS

Chinese Office Action issued in Application No. 202210849509.8 dated Sep. 29, 2023.
(Continued)

*Primary Examiner* — Vivian C Chin
*Assistant Examiner* — Douglas J Suthers
(74) *Attorney, Agent, or Firm* — KED & ASSOCIATES, LLP

(57) ABSTRACT

Provided is a mask apparatus. The mask apparatus includes a mask body in which a microphone and a speaker are installed, a face guard coupled to a rear surface of the rear body so as to be in close contact with a user's face and having a breathing space therein, a pressure sensor installed in the mask body to measure a pressure of the breathing space, and a controller configured to compare a current pressure value measured by the pressure sensor to a reference pressure value and control a voice output of the speaker based on a difference between the current pressure value and the reference pressure value.

18 Claims, 16 Drawing Sheets

(51) Int. Cl.
*H04R 1/02* (2006.01)
*H04R 1/08* (2006.01)

(58) Field of Classification Search
USPC .......................................... 381/301
See application file for complete search history.

(56) References Cited

U.S. PATENT DOCUMENTS

| | | | |
|---|---|---|---|
| 10,827,244 | B1 | 11/2020 | Ward et al. |
| 11,222,648 | B1 * | 1/2022 | Hansen ............... A61M 16/024 |
| 2010/0322442 | A1 | 12/2010 | Namm |
| 2015/0165140 | A1 | 6/2015 | Cappelli et al. |
| 2017/0296094 | A1 | 10/2017 | Fonzi, III et al. |

FOREIGN PATENT DOCUMENTS

| | | |
|---|---|---|
| CN | 108885819 | 11/2018 |
| CN | 111135411 | 5/2020 |
| JP | 2015-163090 | 9/2015 |
| JP | 2018-143702 | 9/2018 |

OTHER PUBLICATIONS

European Search Report dated Nov. 25, 2022 issued in Application No. 22182199.4.

\* cited by examiner (A)

(b)

(A)

(b)

MASK APPARATUS AND METHOD FOR CONTROLLING THE SAME

CROSS-REFERENCE TO RELATED APPLICATIONS

The present application claims priority under 35 U.S.C. 119 and 35 U.S.C. 365 to Korean Patent Application No. 10-2021-0093999 (filed on Jul. 19, 2021), which is hereby incorporated by reference in its entirety.

BACKGROUND

The present disclosure relates to a mask apparatus and a method for controlling the same.

A mask may be defined as a hygiene product that covers the user's nose and mouth to filter harmful substances including germs and dust contained in the air when the user inhales and minimize spreads of virus or bad breath discharged when the user exhales to nearby people.

Recently, as the virus that is highly spreadable and highly contagious has spread, it is recommended that individuals wear a mask to go out for safety in order to minimize transmission.

Currently, various types and forms of masks are released in the market, and in particular, in order to minimize the harmful substances contained in the air from directly entering the mask wearer's respiratory tract, a lot of masks equipped with a filter module are being sold.

In addition, in order to facilitate a flow of air passing through the mask when the user inhales or exhales, a mask equipped with a fan is also being on sale.

Chinese Patent 103127633, which is the prior art document, (published on Jun. 5, 2013) discloses a multi-functional mask provided with a community system.

The mask disclosed in the prior art document includes a mask body provided with a filter, an amplification module coupled to the mask body, a communication module, a lighting module, and a help calling module.

Specifically, the mask is configured to cover a user's face, and each of modules performing various functions is installed on a front surface of the mask. When a user wears the mask, external air of the mask passes through the filter and is purified and then flows into the mask, and the introduced purified air may be guided to the user's respiratory tract.

In addition, in a state in which the mask is worn, the user may improve community convenience by using at least one of the amplification module, the communication module, the lighting module, or the help call module.

Particularly, when the user has a conversation while wearing the mask, a voice may be amplified by the amplification module and then output through a speaker. Thus, even in a state in which the face is covered by the mask, the voice in a sealed space may be output to the outside of the mask in the amplified state.

However, the multi-functional mask disclosed in the prior art document has the following limitations.

First, the mask according to the related art does not support a voice amplification function according to breathing characteristics to cause inconvenience in use of the mask.

Specifically, in the mask according to the related art, the voice amplification function is not turned on or off according to the user's breathing characteristics. For example, in the conventional mask, it is inconvenient that, if power of the mask is turned on, the voice amplification function is activated, or if the voice amplification function is not desired, the voice amplification function is turned off (deactivated) through a separation operation.

If the voice amplification function is activated even when the user does not have a conversation, there is a limitation in that breathing sound or fan noise is input to the microphone, and breathing sound or the fan noise is amplified and output to the outside.

That is, when the user is talking, the voice amplification function needs to be activated, and when the user is not talking, the voice amplification function needs to be deactivated.

Second, the mask according to the related art has a limitation in that the conversation is not smooth due to unnecessary noise.

For example, when having the conversation while wearing the mask, there is a limitation in that not only voice but also breathing sound is inputted to the microphone, and thus, the voice is not clearly output.

Specifically, the mask may have a shape that covers a person's face so as to cover the person's respiratory system (nose or mouth). In addition, the mask may have a compact size and design to improve portability. Here, the microphone may be disposed adjacent to the respiratory tract to more accurately receive the user's voice.

However, when the microphone is installed around the respiratory tract to increase in voice recognition rate, there is a limitation in that the breathing sound is directly input into the microphone to generate unnecessary noise.

If the microphone is installed at a point that is far from the respiratory tract, there is a limitation in that the voice is not accurately recognized because the voice is not directly input to the microphone, and noise is mixed.

Third, the mask according to the related art has a limitation in that a sound output from a speaker is input to the microphone to generate noise according to a howling phenomenon.

Specifically, due to the structure of the compact mask, the microphone and the speaker may be disposed adjacent to each other or disposed in the same sealed space. In this case, there is a limitation in that the voice output from the speaker is input to the microphone adjacent to the speaker, resulting in noise due to howling in the speaker.

SUMMARY

Embodiments provide a mask apparatus capable of turning on or off a voice amplification function according to user's breathing characteristics, and a method for controlling the same.

Embodiments also provide a mask apparatus capable of clearly outputting a voice while wearing a mask, and a method for controlling the same.

Embodiments also provide a mask apparatus capable of automatically converting a voice output function without a separate operation according to a user's breathing state, and a method for controlling the same.

Embodiments also provide a mask apparatus capable of clearly outputting a voice by correcting a portion different from an actual original sound for each frequency, and a method for controlling the same.

Embodiments also provide a mask apparatus capable of preventing noise due to a howling phenomenon from occurring, and a method for controlling the same.

Embodiments also provide a mask apparatus capable of preventing a breathing sound and fan noise input to a microphone from being output to the outside through a speaker, and a method for controlling the same.

In one embodiment, a mask apparatus includes: a mask body in which a microphone and a speaker are installed; a face guard coupled to a rear surface of the rear body so as to be in close contact with a user's face and having a breathing space therein; a pressure sensor installed in the mask body to measure a pressure of the breathing space; and a controller configured to compare a current pressure value measured by the pressure sensor to a reference pressure value and control a voice output of the speaker based on a difference between the current pressure value and the reference pressure value.

The controller may determine user's breathing characteristics or breathing state through the pressure sensor to activate (ON) or deactivate (OFF) the voice output of the speaker according to the determined breathing state.

Specifically, as the result of determining the breathing state, the voice output of the speaker may be activated during an exhalation section, and the voice output of the speaker may be deactivated during an inspiration second, and thus, the user's voice may be amplified and output during utterance. Therefore, there is an advantage that the voice is clearly output during the utterance while wearing the mask.

In addition, since the voice output is activated only in the utterable period, and the voice output is inactivated in the non-utterable period, use convenience may be improved during the utterance, and breathing sound or fan noise may be prevented from being output during non-utterance. Thus, there may be an advantage that an effective conversation is performed.

In addition, since a voice amplification function is automatically converted on or off without a separate operation, mask touch may be reduced, which is convenient, and a sanitary condition of the mask may be improved.

The control of the voice output of the speaker may include adjusting an input signal level of the voice signal input from the microphone or muting the voice signal input from the microphone.

The reference input value may be an intermediate value between a maximum pressure value and a minimum pressure value among pressure values measured for a predetermined time by the pressure sensor. For example, the reference pressure value may be an intermediate value between a maximum pressure value and a minimum pressure value among pressure values measured in once breathing cycle.

The reason for defining the reference pressure value as the intermediate value between the maximum pressure value and the minimum pressure value among the measured pressure values may be for more accurately estimating the user's breathing state.

In this embodiment, if the current pressure value is greater than the reference pressure value, it may be determined that the exhaling state (utterable state), and if the current pressure value is less than the reference pressure value, it may be determined that the inhaling state (non-utterable state).

When the measured current pressure value is less than the reference pressure value, the controller may be configured to deactivate a voice output function of the speaker or mute a voice.

As a result of the determination, if the user's breathing state is the inhalation section, it may be determined that utterance is impossible, and accordingly, the voice output function of the speaker may be turned off. Thus, it may be possible to prevent the breathing sound or fan noise from being output to the speaker.

When the measured current pressure value is greater than the reference pressure value, the controller may be configured to activate a voice output function of the speaker or release a mute state.

As a result of the determination, if the user's breathing state is an exhalation section, it may be determined that utterance is possible, and accordingly, the voice amplification function of the speaker may be turned on. Therefore, during the utterance while wearing the mask, the voice may be effectively amplified and output, and the use convenience may be improved.

The mask apparatus may further include a voice processing module configured to convert a voice signal input from the microphone into an electrical signal and provide the converted electrical signal into the speaker.

When the measured current pressure value is greater than the reference pressure value, the voice processing module may be configured to give a predetermined frequency characteristic with respect to the voice signal input from the microphone so as to compensate an input signal level of the voice signal.

For example, during the user's utterance, a voice signal input through the microphone may be distorted by various factors and output as it is. In this case, the output voice signal may have a limitation of showing characteristics different from the actual voice.

To solve this limitation, the voice processing module may apply an equalizer to the input voice signal to correct a portion different from the actual original sound for each frequency.

When the measured current pressure value is greater than the reference pressure value, the voice processing module may be configured to restrict an output of an input signal having an input signal level greater than a first level among input signals input from the microphone.

For example, a howling phenomenon may occur because the microphone and the speaker are close to each other due to the structural characteristics of the mask. In this case, the voice signal output from the speaker may be input to the microphone, amplified by the amplifier, and output to the speaker.

To prevent this limitation, the voice processing module may apply a compressor that restricts the output by setting a critical value so that the input signal level of the input voice signal does not increase above a certain level.

When the measured current pressure value is greater than the reference pressure value, the voice processing module may be configured to block an output of an input signal having an input signal level less than a second level among voice signals input from the microphone.

For example, the fan noise, which is generated while a fan installed in the mask is driven, and the user's breathing sound may be input to the microphone, amplified by the amplifier, and output to the speaker.

To prevent the limitation, the voice processing module may apply a noise gate that blocks an output of the input signal of which an input signal level is less than a predetermined level among the input voice signals.

The mask apparatus may further include a communication module provided to the mask body to communicate with an external device, wherein the speaker may be controlled by the external device. Thus, the speaker may be remotely controlled by an external device, and thus there may be an advantage in that manipulation convenience is improved.

In another embodiment, a method for controlling a mask apparatus includes: measuring a current pressure value with respect to a mask by using the pressure sensor; comparing the measured current pressure value to a reference pressure value; and controlling a voice output of the speaker based on a difference between the current pressure value and the reference pressure value.

The details of one or more embodiments are set forth in the accompanying drawings and the description below. Other features will be apparent from the description and drawings, and from the claims.

DETAILED DESCRIPTION OF THE EMBODIMENTS

Reference will now be made in detail to the embodiments of the present disclosure, examples of which are illustrated in the accompanying drawings.

In the following detailed description of the preferred embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense.

Also, in the description of embodiments, terms such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, the former may be directly "connected," "coupled," and "joined" to the latter or "connected", "coupled", and "joined" to the latter via another component.

Figure 1:
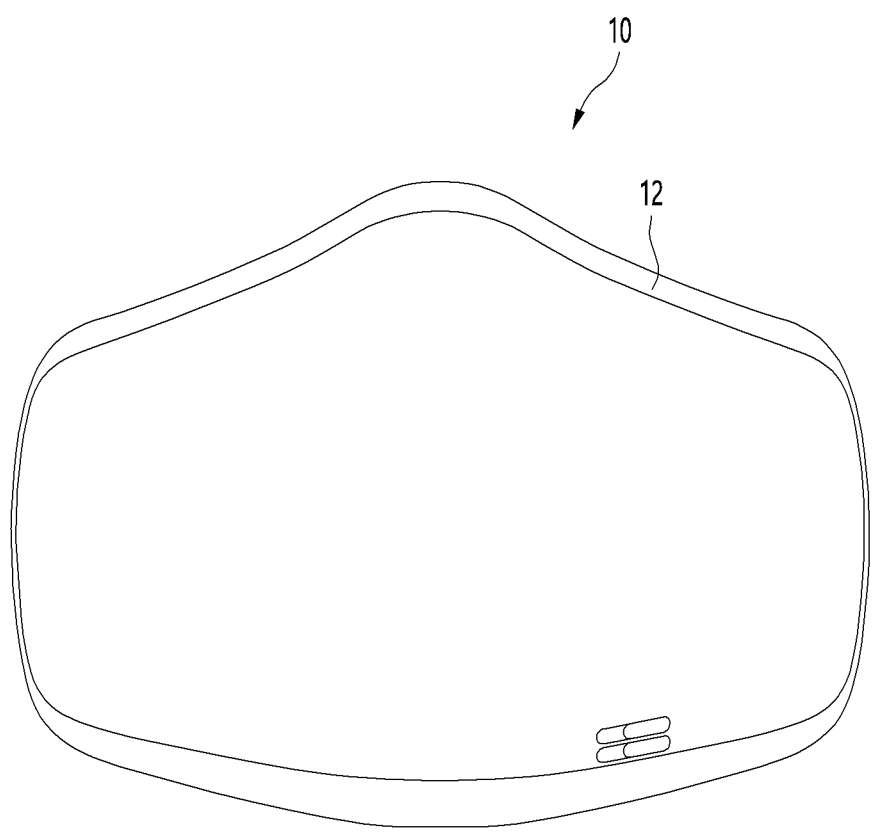
FIG. 1 is a front view of a mask apparatus according to an embodiment.
Figure 2:
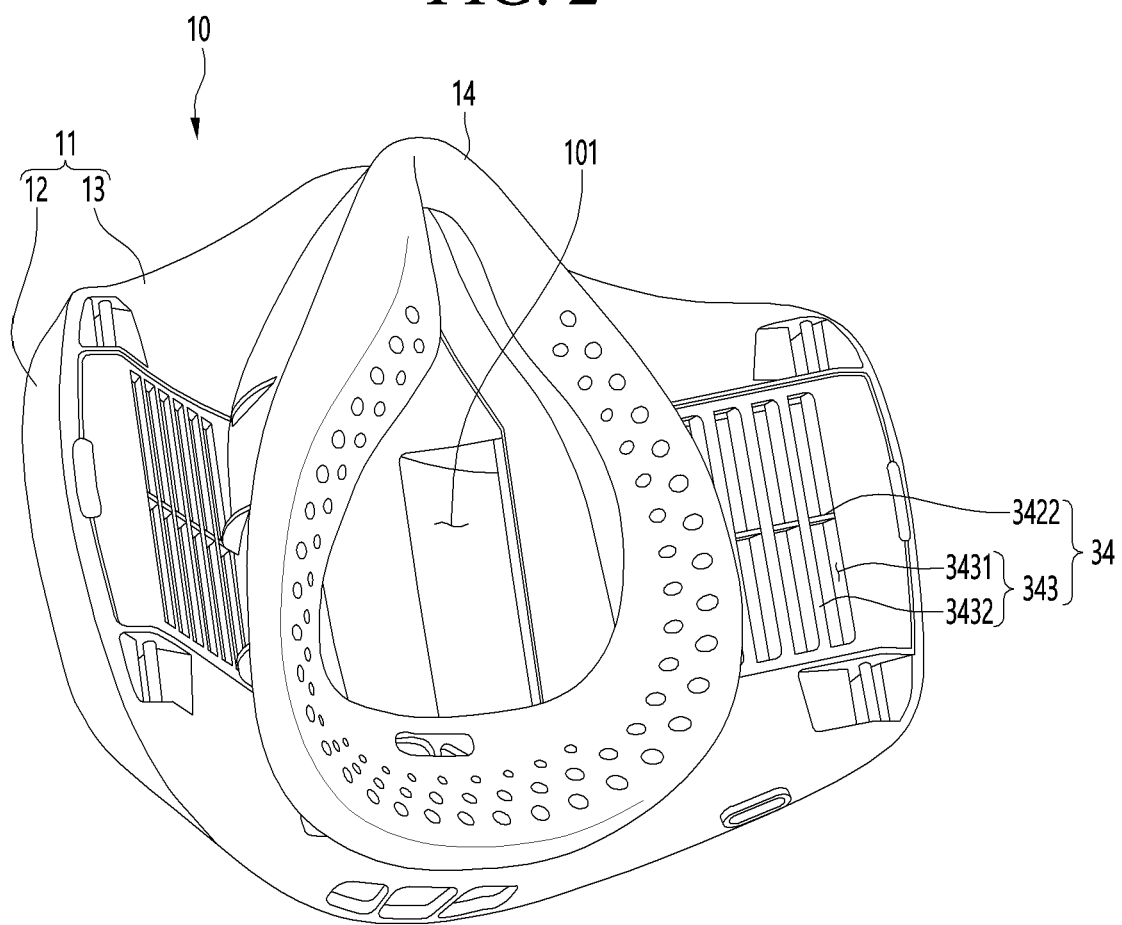
FIG. 2 is a rear perspective view of the mask apparatus.
Figure 3:
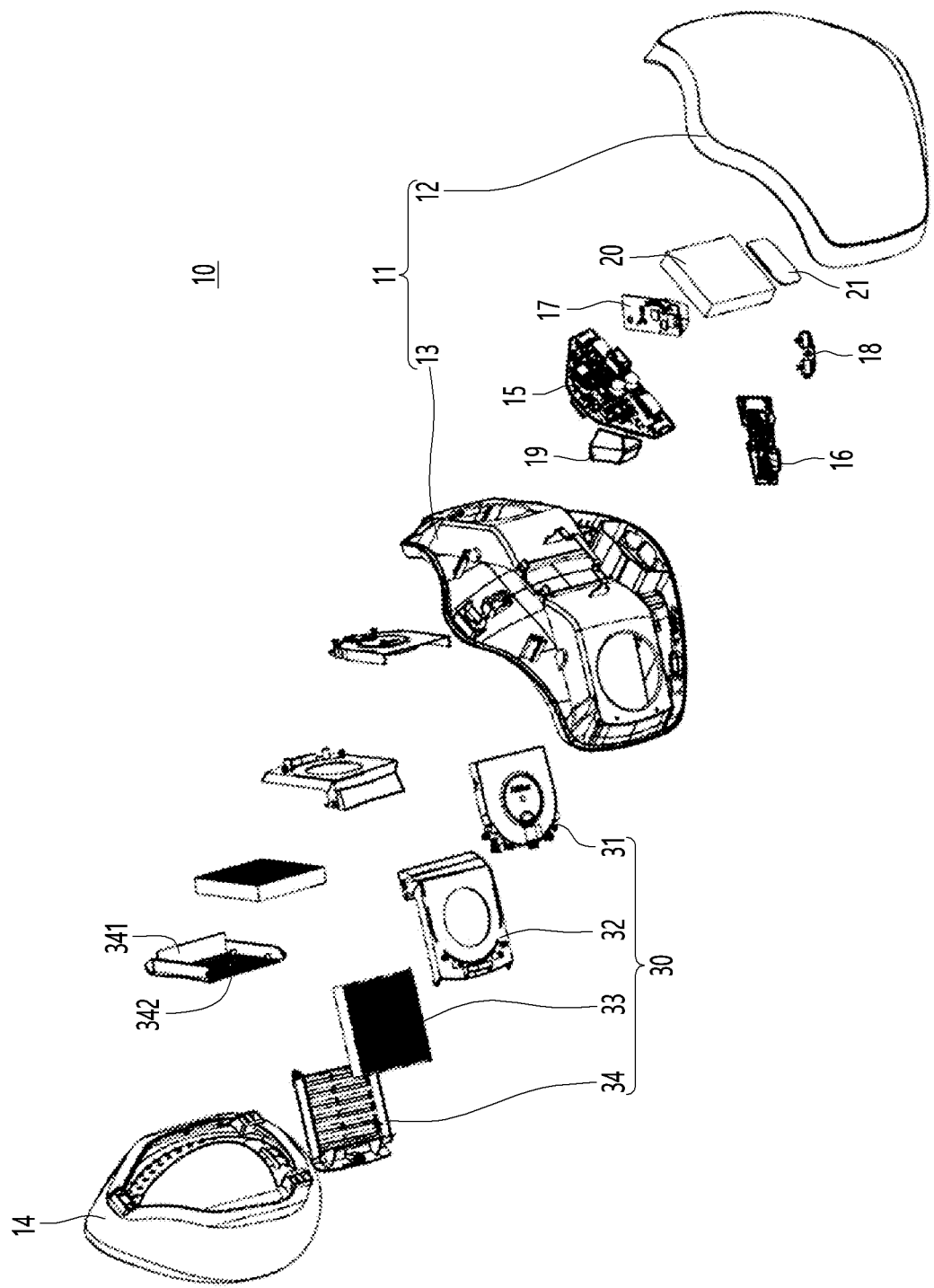
FIG. 3 is an exploded perspective view of the mask apparatus.
Figure 4:
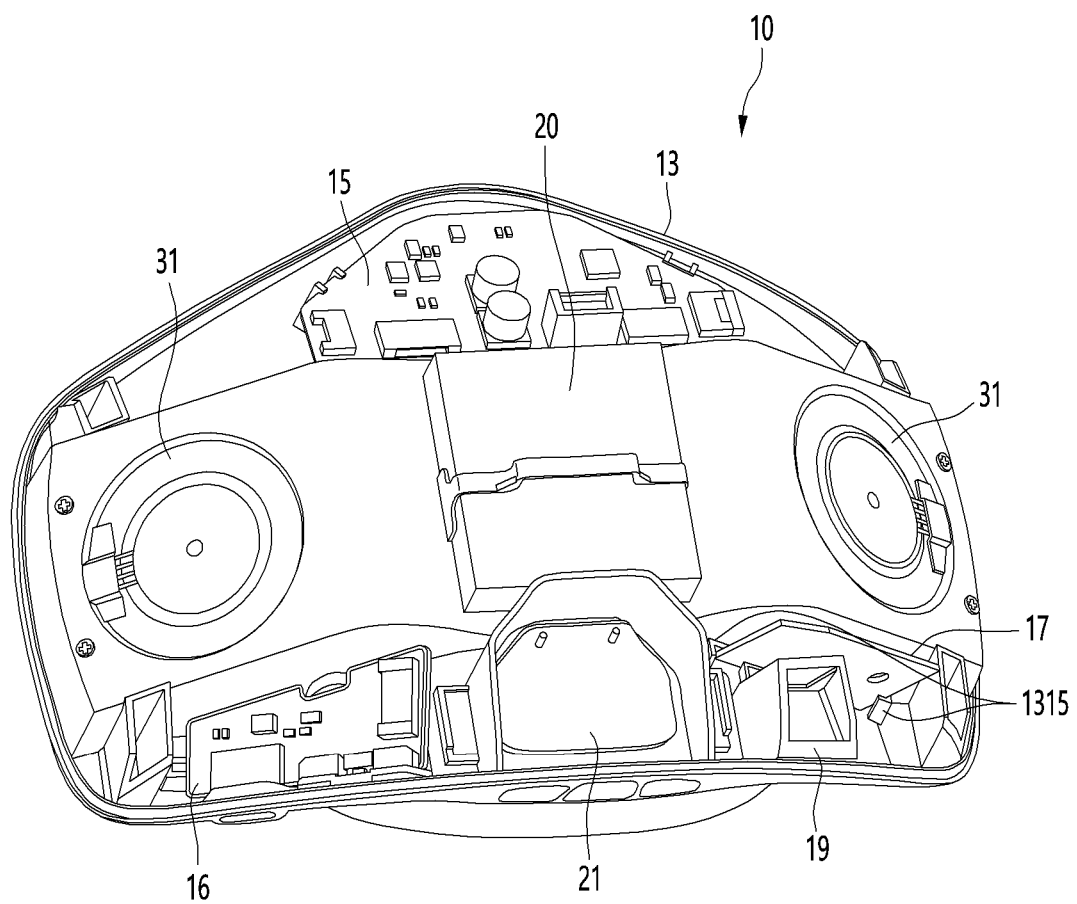
FIG. 4 is a front perspective view of the mask apparatus from which a front body is separated.

FIG. 1 is a front view of a mask apparatus according to an embodiment, FIG. 2 is a rear perspective view of the mask apparatus, FIG. 3 is an exploded perspective view of the mask apparatus, and FIG. 4 is a front perspective view of the mask apparatus from which a front body is separated.

Referring to FIGS. 1 to 4, a mask apparatus 10 according to an embodiment includes a mask body 11, a face guard 14 that is fixedly or detachably coupled to a rear surface of the mask body 11, and an air cleaning module 30 mounted inside the mask body 11.

In detail, the mask body 11 includes a front body 12 defining an outer appearance of a front surface and a rear body 13 coupled to a rear surface of the front body 12 to define an outer appearance of a rear surface. The front surface of the front body 12 defines a front surface of the mask apparatus 10, and the rear surface of the rear body 13 faces a face of a user (or a wearer).

In addition, the face guard 14 may be coupled to the rear surface of the rear body 13 so as to be in close contact with the user's face and may be made of a silicone or rubber material having elasticity. A breathing space is defined inside the face guard 14, and when the user wears the mask apparatus 10, a user's nose and mouth are accommodated in the breathing space. Thus, external air purified while passing through the air cleaning module 30 is guided to the breathing space and inhales by the user, and air generated when the user exhales is also discharged into the breathing space.

A predetermined space is defined between the front body 12 and the rear body 13, and as illustrated in FIG. 4, various electrical components are mounted on the front surface of the rear body 13. In addition, the various electrical components are shielded by the front body 12 so as not to be exposed to the outside.

In addition, the air cleaning module 30 includes a fan module 31 placed in an accommodation portion 133 (see FIG. 6) provided in the rear body 13 and a filter 33 placed behind the fan module 31. The fan module 31 includes a centrifugal fan that suctions air in an axial direction to discharge the air in a radial direction.

The air cleaning module 30 further includes a filter housing 34 disposed behind the filter 33, and a suction hole through which external air is suctioned is defined in the filter housing 34. The filter housing 34 may be rotatably coupled to the rear body 13, and the suction hole may be provided in the form of a suction grill 343 as illustrated in the drawings.

In detail, the filter housing 34 includes a filter frame 341 surrounding three side surfaces of the filter 33, and a filter cover 342 disposed on a rear surface of the filter frame 341. The filter cover 342 includes a suction grill 343.

The suction grill 343 may be understood as a structure including a plurality of suction slits 3431 and a plurality of partition ribs 3432 disposed between the adjacent suction slits 343. The suction grill 343 may be understood as a structure in which one large suction hole is divided into a plurality of narrow and long suction slits 3431 by the plurality of partition ribs 3432. In addition, the plurality of narrow and long suction slits 3431 may be divided into an upper slit and a lower slit by a reinforcing rib 3422. Hereinafter, the suction hole defined in the rear surface of the mask apparatus 10 to suction the external air is defined as including various types of holes including the suction grill 343, and the suction hole of the mask body 11 and the suction grill 343 should be interpreted as the same meaning.

In addition, a discharge hole 101 is defined at a point spaced apart from the suction hole in a central direction of the rear body 13. The external air suctioned through the suction hole or the suction grill 343 by an operation of the fan module 31 sequentially passes through the filter 33 and the fan module 31 and then is discharged into the breathing space through the discharge hole 101.

The suction hole, i.e., the suction grill 343 is disposed outside the face guard 14, and the discharge hole 101 is disposed inside the face guard 14. That is, the suction grill 343 is disposed outside the breathing space, and the discharge hole 101 is defined inside the breathing space, and thus, the suctioned external air and the air exhaled by the user are not mixed with each other.

The air cleaning module 30 further includes a flow guide 32 disposed behind the fan module 31.

In addition, the mask apparatus 10 further includes at least one of a main control module 15, a power module 16, an indicator module 18, a wireless communication module 17, a speaker module 19, and a battery 20, or an exhaust valve 21.

In detail, the main control module 15 is a module for controlling operations of the fan module 31, the speaker module 19, and a pressure sensor and a microphone, which will be described later. The main control module 15 may be disposed on an upper portion of a center of the front surface of the rear body 13.

The power module 16 is a control module for supplying power to the electric components mounted on the mask apparatus 10. The power module 16 may be disposed at a right lower end of the front surface of the rear body 13.

A cable connector, into which a terminal of a cable for power supply and data transmission is inserted, and an LED module used to inform an operation state of the mask apparatus 10 may be mounted on the power module 16. Then, light irradiated from the LED module is diffused and guided through the indicator module 18 and then is emitted to the outside of the mask apparatus 10.

The wireless communication module 17 may be any one of various types of short-range wireless communication modules including Bluetooth. The wireless communication module 17 may be disposed on a left lower end of the front surface of the rear body 13. The wireless communication module 17 may be mounted on the front surface of the rear body 13 in a direction crossing the rear body 13, for example, horizontally. The wireless communication module 17 may be mounted on the front surface of the rear body 13 in a horizontal state by a pair of substrate insertion ribs 1315 protruding from the front surface of the rear body 13. Both side ends of the wireless communication module 17 are supported by the pair of substrate insertion ribs 1315.

The speaker module 19 may be disposed on the left lower end of the front surface of the rear body 13 corresponding to a lower side of the wireless communication module 17.

The battery 20 may be disposed at a center of the front surface of the rear body 13, and the exhaust valve 21 may be disposed to shield an exhaust port provided below the center of the front surface of the rear body 13. That is, when the user exhales, the exhaust valve 21 may open the exhaust port, and when the user inhales, the exhaust valve 21 may block the exhaust port. The exhaust valve 21 may be bent and provided in the form of a flat flap.

Here, it should be noted that the front, rear, left, and right sides of the mask body 11 are defined based on a state in which the user wears the mask apparatus 10.

Figure 5:
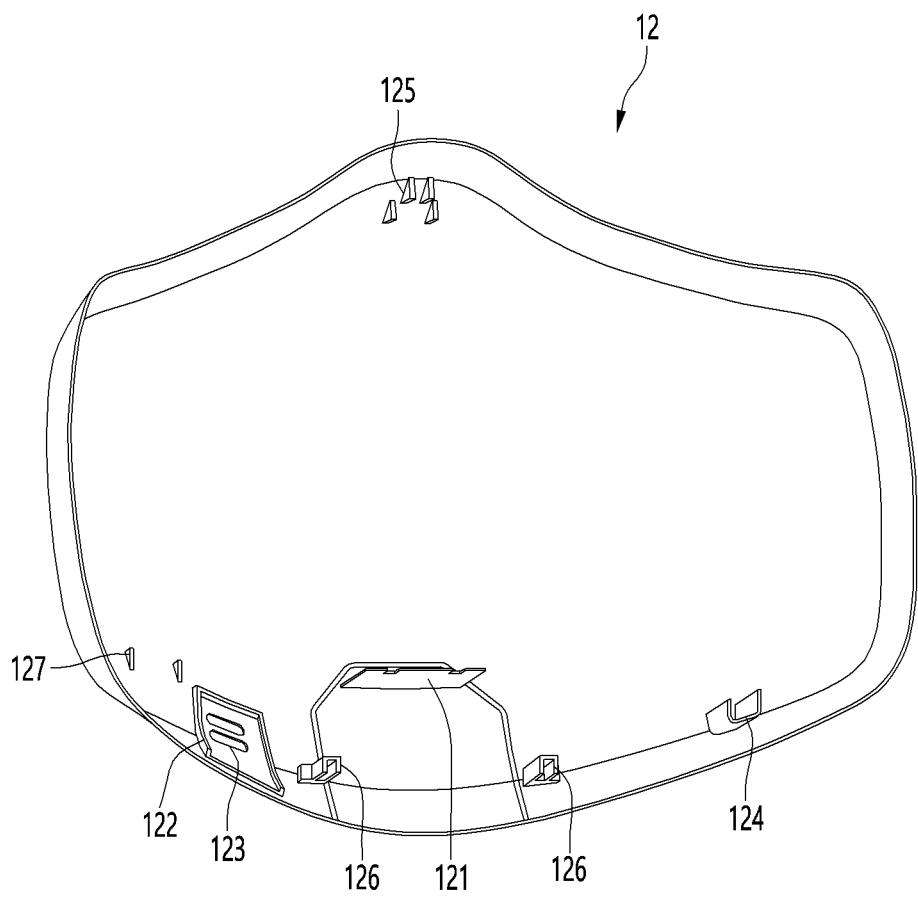
FIG. 5 is a rear perspective view of a front body constituting the mask apparatus according to an embodiment.

FIG. 5 is a rear perspective view of the front body constituting the mask apparatus according to an embodiment.

Referring to FIG. 5, the front body 12 constituting the mask apparatus 10 according to the embodiment defines an outer appearance of the front surface of the mask apparatus 10.

When the front surface of the front body 12 is provided as a single body without a separate component mounted thereon, it has the advantage of being clean in outer appearance. When the suction hole is defined at each of the left and right sides of the front body 12, if the suction hole is placed to face an upper side after taking off the mask apparatus 10, there is disadvantage in that possibility, in which foreign substances are introduced into the mask apparatus 10 through the suction hole, is high.

In addition, when a separate cover is installed to shield the suction hole, thereby minimizing the inflow of the foreign substances, a gap needs to be defined between an edge of the cover and the front surface of the front body 12 so that external air is introduced. That is, there is a restriction that the separate cover has to be coupled to the front surface of the front body 12 in the form that protrudes from the front surface of the front body 12.

As a result, there is a high possibility that the separate cover is damaged by external force or be separated from the front body 12 by being caught by a surrounding obstacle. For this reason, it is advantageous in appearance to design the front body 12 so that the suction hole for inhaling the external air is not defined as much as possible to prevent a separate component from protruding due to additional mounting of the separate component on the front surface of the front body 12, and also it is advantageous for securing durability.

In consideration of this aspect, the suction hole for suctioning the external air is not defined in the front surface of the front body 12 according to the embodiment of the present invention, and also, additional components including the cover are not mounted at all, and thus, the front surface is designed so that a smooth and continuous single surface is provided. However, a speaker hole 123 is defined in a side of the lower portion so that user's voice is output to the outside.

A plurality of protrusion structures are disposed on the rear surface of the front body 12.

In detail, one or plurality of substrate fixing ribs 125 protrude from an upper end of the center of the rear surface of the front body 12. The one or plurality of substrate fixing ribs 125 may press a front surface of the main control module 15 mounted on the rear body 13 when an edge of the front body 12 is coupled to an edge of the front surface of the rear body 13 to prevent the main control module 15 from being oscillated.

A valve support rib 121 horizontally protrudes from the rear surface of the front body 12. The valve support rib 121 is disposed at a point at which an upper end of the exhaust valve 21 is disposed when the front body 12 is coupled to the rear body 13, to press an upper end of a front surface of the exhaust valve 21. For example, the valve support rib 121 may have a predetermined width and extend backward by a predetermined length at a point spaced a predetermined distance downward from the center of the rear surface of the front body 12.

In addition, a pair of magnet pressing ribs 126 may protrude from the rear surface of the front body 12. In detail, the face guard 14 is mounted on the rear surface of the rear body 13, a magnet is mounted on a front surface of the face guard 14, and a magnet that is attractive to the magnet is mounted on the front surface of the rear body 13. As a result, the face guard 14 is detachably mounted on the rear surface of the rear body 13 by the magnetic force of the magnet.

At this time, a pair of lower magnet mounting portions 135 (see FIG. 6) for mounting the magnet are disposed on the front surface of the rear body 13. In addition, the pair of magnet pressing ribs 126 function to press the pair of magnets mounted on the pair of lower magnet mounting portions 135, respectively.

In addition, a substrate pressing rib 127 that is in contact with a front end of a substrate constituting the wireless communication module 17 protrudes from the rear surface of the front body 12. In detail, when the front body 12 and the rear body 13 are coupled to each other, the substrate pressing rib 127 presses the front end of the substrate constituting the wireless communication module 17 to prevent the wireless communication module 17 from being oscillated or being separated from the substrate insertion rib 1315.

In addition, a support rib 122 supporting and surrounding an edge of the front end of the speaker module 19 is disposed on the rear surface of the front body corresponding to an edge of the speaker hole 123. The support rib 122 may be surrounded in a shape corresponding to a shape of the front surface of the speaker module 19.

In addition, a substrate fixing rib 124 for pressing a front surface of the power module 16 protrudes from the rear surface of the front body 12. The substrate fixing rib 124 presses a front surface of the substrate constituting the power module 16 to prevent the power module 16 from oscillated or being separated from the rear body 13.

Figure 6:
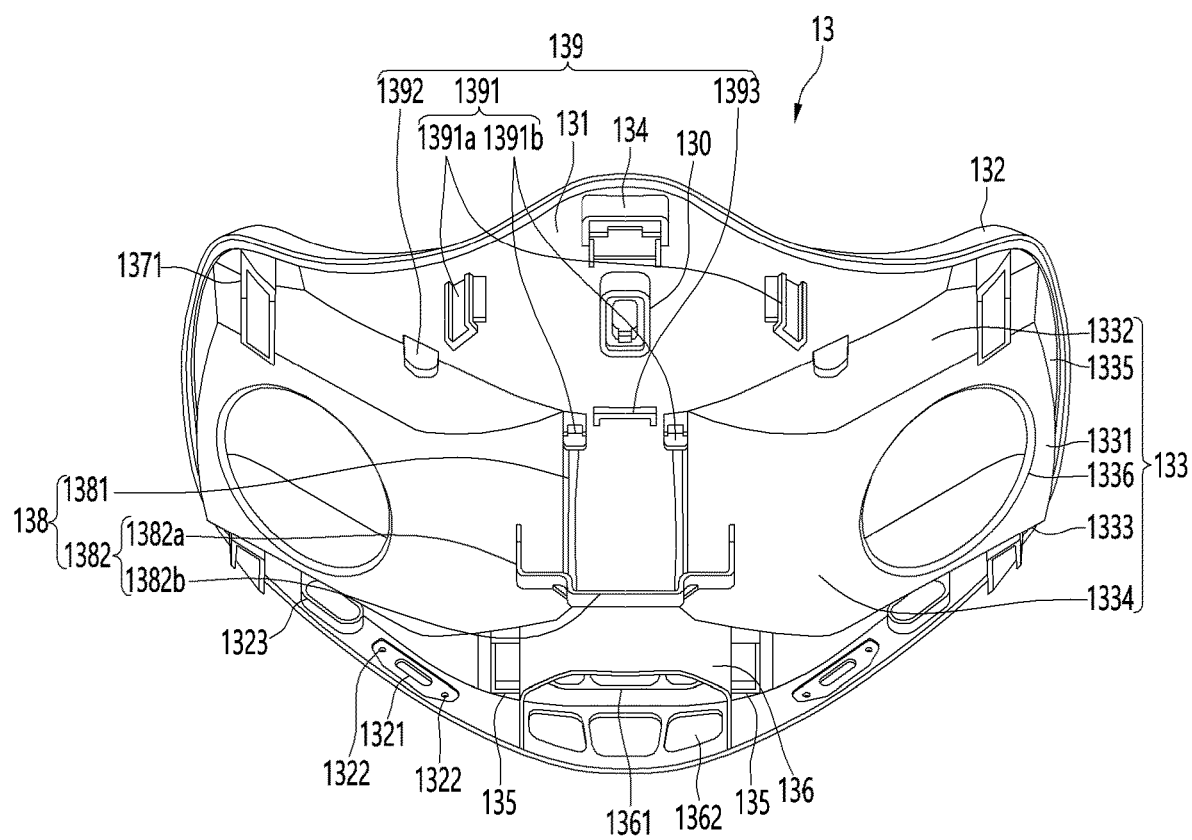
FIG. 6 is a front perspective view of a rear body constituting the mask apparatus according to an embodiment.
Figure 7:
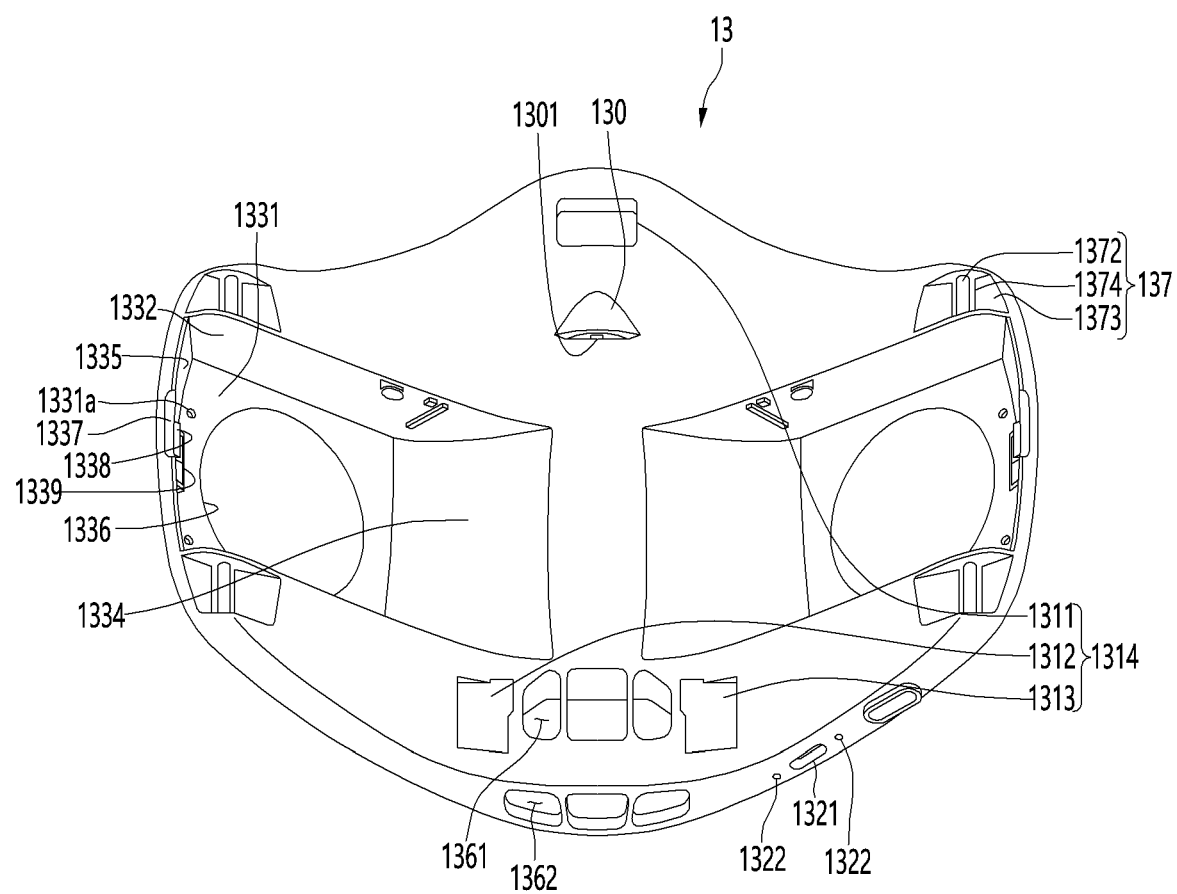
FIG. 7 is a rear perspective view of the rear body.

FIG. 6 is a front perspective view of the rear body constituting the mask apparatus according to an embodiment, and FIG. 7 is a rear perspective view of the rear body.

Referring to FIGS. 6 and 7, the rear body 13 constituting the mask apparatus 10 according to the embodiment includes a face cover portion 131 that covers a user's face and a fusion portion 132 bent forward from an edge of the face cover portion 131.

In detail, the fusion portion 132 is continuously disposed along an edge of a top surface, edges of both surfaces, and an edge of a bottom surface of the face cover portion 131. In addition, a width of the fusion portion 132 in a front and rear direction, which is bent along an edge of a bottom surface of the face cover portion 13 to extend forward is the largest.

In the fusion portion 132, a portion disposed on the edge of the bottom surface of the face cover portion 131 may be specifically defined as an extension protrusion. The extension protrusion has a convexly rounded shape in such a manner that a width in the front and rear direction gradually increases from both side ends of the rear body 13 toward the center.

A bottom surface exhaust hole 1362 is disposed at a center of the fusion portion 132 defined as the extension protrusion, and a button hole 1321 is defined at a point spaced apart from the bottom exhaust port 1362 toward a side end of the rear body 13. A power button is inserted into the button hole 1321. An indication hole 1322 is defined at a point spaced apart from each of left and right edges of the button hole 1321.

Light irradiated from a light emitting unit mounted on the power module 16 is emitted to the outside through the pair of indication holes 1322. The light emitting unit includes an LED module.

When the light is emitted to the outside through any one of the pair of indication holes 1322, it may mean that the power of the mask apparatus 10 is turned on. In addition, a remaining amount of battery 20 may be predicted according to a color of the light emitted through the other one of the pair of indication holes 1322.

A terminal insertion hole 1323 is defined at a point further spaced apart from the button hole 1321 toward the side end of the rear body 13. A universal serial bus (USB) cable may be inserted into a terminal connector provided in the power module 16 through the terminal insertion hole 1323. The battery 20 is charged through the USB cable, and a version or function of the mask apparatus 10 may be updated or upgraded by data transmitted through the USB cable.

A accommodation portion 133 for accommodating the air cleaning module 30 is provided in the rear body 13. The accommodation portion 133 is provided at each of left and right sides from the center of the rear body 13, and the pair of accommodation portions 133 are symmetrical with respect to a vertical line passing through the center of the rear body 13.

The accommodation portion 133 protrudes forward from the front surface of the face cover portion 131 to define a space in which the air cleaning module 30 is accommodated. The accommodation portion 133 includes a seating surface 1331 on which the air cleaning module 30, specifically, the fan module 31 is seated, a coupling surface 1335 connecting an outer edge of the seating surface 1331 at a side end of the face cover portion 131, and an air guide surface 1334 connecting the front surface of the face cover portion 131 at an inner edge of the seating surface 1331.

In addition, the accommodation portion 133 further include a top surface 1332 connecting upper ends of the seating surface, the air guide surface 1334, and the coupling surface 1335 to the front surface of the face cover portion 131. In addition, the accommodation portion 133 further include a bottom surface 1333 connecting lower ends of the seating surface, the air guide surface 1334, and the coupling surface 1335 to the front surface of the face cover portion 131.

One or more coupling units, for example, coupling hooks, are disposed on the coupling surface 1335.

A fan mounting hole 1336 may be defined in the seating surface 1331, and the top surface 1332 and the bottom surface 1333 may extend horizontally and extend parallel to each other.

The coupling surface 1335 may be convexly rounded toward the outside of the rear body 13 and be inclined toward the center of the rear body 13 from the face cover portion 131 to the seating surface 1331.

The air guide surface 1334 may be designed to extend convexly and roundly from the seating surface 1331 toward the face cover portion 131 so that air suctioned by the fan module 31 is smoothly guided toward the discharge hole 101 along the air guide surface 1334.

As another example, the air guide surface 1334 is constituted by a round portion that is rounded with a predetermined curvature at the inner edge of the seating surface 1331 and an inclined portion connecting the face cover portion 131 flatly and obliquely at an end of the round portion.

The accommodation portion 133 includes a left accommodation portion disposed at the left side from the center of the rear body 13 and a right accommodation portion disposed at the right side from the center of the rear body 13. The left accommodation portion and the right accommodation portion are spaced a predetermined distance from the center of the rear body 13, and the battery 20 is mounted in a space between the left accommodation portion and the right accommodation portion.

A battery mounting portion 138 may be disposed on the front surface of the rear body 13. In detail, the battery mounting portion 138 includes a pair of battery seating ribs 1381 and a battery support rib 1382.

The pair of battery seating ribs 1381 protrude forward from the front surface of the face cover portion 131 or an edge of the air guide surface 1334 to extend in parallel in the vertical direction. The pair of battery seating ribs 1381 supports a rear surface of the battery 20.

One end of the battery support rib 1382 extends from either one of the left air guide surface 1334 and the right air guide surface 1334, and the other end is connected to the other side of the left air guide surface 1334 and the right air guide surface 1334.

The battery support rib 1382 has an n-shape to support the front and both surfaces of the battery 20. Thus, a phenomenon in which the battery 20 is separated from the rear body 13 may be prevented by the battery support rib 1382.

In addition, a central portion of the battery support rib 1382 protrudes forward so that a battery having a different size is selectively mounted.

In detail, the battery support rib 1382 includes a pair of extension portions extending forward from the pair of air guide surfaces 1334 and a connection portion extending in a horizontal direction to connect the pair of extension portions to each other.

In addition, a portion of the connection portion is bent to extend forward, so that the battery support rib 1382 is described as being constituted by a first battery support 1382a and a second battery support 1382b. In detail, the first battery support 1382a may be used to support a relatively wide and thin battery, and the second battery support 1382b may be used to support a relatively narrow and thick battery.

The second battery support 1382b may be described as being provided by bending a portion of the connection portion constituting the first battery support 1382a forward a plurality of times. Alternatively, it may be described that the relatively small n-shaped second battery support 1382b protrudes from a front surface of the relatively large n-shaped first battery support 1382a.

An exhaust passage guide 136 protrudes forward from the front surface of the face cover portion 131 corresponding to a lower side of the battery mounting portion 138. In detail, the exhaust passage guide 136 is disposed below the battery mounting portion 138, and a lower end of the battery 20 mounted on the battery mounting portion 138 is supported by a top surface of the exhaust passage guide 136. As a result, it is possible to prevent the battery 20 from being pulled downward due to gravity while being inserted into the battery mounting portion 138.

The exhaust passage guide 136 may have a substantially tunnel-shaped longitudinal cross-section, and a front exhaust port 1361 may be disposed on the face cover portion 131 corresponding to the inside of the exhaust passage guide 136.

At least one of the front exhaust port 1361 or the bottom exhaust port 1362 may be provided in the form of an exhaust grill divided into a plurality of small exhaust ports by a plurality of grills or partition ribs. In addition, the front exhaust port 1361 is selectively opened and closed by the exhaust valve 21.

An upper magnet mounting portion 134 is disposed at the upper end of the center of the front surface of the face cover portion 131, and a pair of lower magnet mounting portions 135 are disposed on a lower end of the front surface of the face cover portion 131.

In detail, the lower magnet mounting portion 135 is disposed on each of a left edge and a right edge of the exhaust passage guide 136. The magnet mounted on the lower magnet mounting portion 135 is pressed by the pair of magnet pressing ribs 126 (see FIG. 5) protruding from the rear surface of the front body 12.

A strap connection portion 137 is disposed at each of the left end and the right end of the rear body 13. In detail, the strap connection portion 137 is a portion to which an end of a strap or band that is caught on the user's ear or wraps around the back of the user's head is connected. The strap connection portion 137 is disposed at each of upper and lower portions of the left and right ends of the rear body 13.

Both ends of any one of the pair of straps may be respectively connected to the strap connection portions 137 provided at the upper left and lower ends, and both ends of the other one may be respectively connected to the strap connection portions 137 provided at the upper right and lower ends. Then, the pair of straps may be hung on both user's ears, respectively.

As another method, both ends of any one of the pair of straps may be respectively connected to the strap connection portions 137 provided at the upper left and right ends, and both ends of the other one may be respectively connected to the strap connection portions 137 provided at the lower left and right ends. Then, the pair of straps may be wrapped around the user's back of the head.

Each of the four strap connection portions 137 includes a strap groove 1373 that is recessed from the front surface of the rear body 13 to extend in the horizontal direction (width direction of the rear body), a strap hole 1374 defined in any point of the strap groove 1373, a strap bar 1372 connecting top and bottom surfaces of the strap groove 1373 to each other, and a tubular waterproof rib 1371 extending from the rear surface of the rear body 13 corresponding to an edge of the strap hole 1374.

A main control module mounting portion 139 is disposed on the front surface of the rear body 13.

In detail, the main control module mounting portion 139 includes a substrate fixing hook 1391 protruding forward from the front surface of the face cover portion 131 and a substrate seating rib 1393 and substrate support rib 1392, which support a rear surface of the main control module 13.

In detail, the substrate fixing hook 1391 may include a pair of first substrate fixing hooks 1391a disposed above the accommodation portion 133 and a pair of second fixing hooks 1391b disposed between the pair of accommodation portions 133 facing each other.

The pair of first substrate fixing hooks 1391a may be disposed at a point spaced upward from a top surface of the left accommodation portion and at a point spaced upward from a top surface of the right accommodation portion. The pair of first substrate fixing hooks 1391a function to fix left and right ends of the main control module 15.

In addition, the pair of second substrate fixing hooks 1391b may be respectively disposed at points corresponding to inner upper ends of the pair of accommodation portions 133. In detail, any one of the pair of second substrate fixing hooks 1391b may be disposed at a point at which an upper edge of the right accommodation portion meets the front surface of the face cover portion 131. In addition, the other of the pair of second substrate fixing hooks 1391*b* may be disposed at a point at which an upper edge of the left accommodation portion meets the front surface of the face cover portion 131.

The pair of second substrate fixing hooks 1391*b* function to fix a lower end of the control substrate constituting the main control module 15.

In addition, the substrate seating rib 1392 may protrude from the front surface of the face cover portion 131 corresponding between the pair of second substrate fixing hooks 1391*b* to support a rear surface of the lower end of the control substrate constituting the main control module 15.

In addition, a rear surface of the upper end of the main control module 15 may be supported by a front end of the upper magnet mounting portion 134. The main control module 15 is disposed to be spaced apart from the face cover portion 131 by the upper magnet mounting portion 134 and the substrate seating rib 1393, and thus, there is an effect that the main control module 15 is stably coupled to the rear body without oscillated by the substrate fixing hook 1391.

A pressure sensor mounting portion (or breathing sensor mounting portion) 130 may be disposed at a center of the upper portion of the front surface of the face cover portion 131. A pressure sensor (to be described later) mounted on the pressure sensor mounting portion 130 senses a pressure in the breathing space defined inside the face guard 14. That is, it may be determined whether the user is currently inhaling or exhaling according to a change in pressure inside the breathing space. The pressure sensor may be defined as a breathing sensor, and although the terms are different, it should be understood as a sensor performing the same function.

The pressure sensor mounting portion 130 is provided on the front surface of the rear body 13, and when the main control module 15 is mounted on the main control module mounting portion 139, the pressure sensor mounting portion 130 is disposed at a point at which the pressure sensor (or breathing sensor) mounted on the rear surface of the main control module 15 is disposed. Thus, when the main control module 15 is mounted to the main control module mounting portion 139, the pressure sensor is accommodated in the pressure sensor mounting portion 130. In addition, a front end of the pressure sensor mounting portion 130 is in close contact with the rear surface of the control substrate of the main control module 15.

In addition, a portion defining a bottom of the pressure sensor mounting portion 130 protrudes to a rear side of the rear body 13, and a through-hole 1301 is defined in a bottom surface of the portion protruding backward. The breathing space defined by the rear surface of the rear body 13 and the face guard 14 and an inner space of the pressure sensor mounting portion 130 communicate with each other through the through-hole 1301. As a result, a portion of air generated when the user exhales flows into the inner space of the pressure sensor mounting portion 130 through the through-hole 1301. In addition, the pressure sensor accommodated in the pressure sensor mounting portion 130 senses a pressure inside the pressure sensor mounting portion 130. In addition, the sensed pressure value is transmitted to a microcomputer (to be described later) of the main control module 15 to determine a user's breathing state or breathing characteristics.

A magnet mounting groove 1314 is defined each of the rear surface of the rear body 13 corresponding to a direct rear surface of the upper magnet mounting portion 134 and the rear surface of the rear body 13 corresponding to a direct rear surface of the pair of lower magnet mounting portions 135.

The magnet mounting groove 1314 includes a first magnet mounting groove 1311 defined in a direct rear surface of the upper magnet mounting portion 134 and a second magnet mounting groove 1312 and a third magnet mounting groove 1313, which are defined in a direct rear surface of the lower magnet mounting portion 134.

Three magnets mounted on the face guard 14 are attached to the first to third magnet mounting grooves 1311 to 1313 by magnetic force, respectively. In addition, when the user pulls the face guard 14 with force greater than the magnetic force, the face guard 14 is easily separated from the rear body 13.

As described above, the fan mounting hole 1336 may be defined in the seating surface 1331 constituting the accommodation portion 133. In addition, one or plurality of flow guide coupling holes 1331*a* are defined at a point spaced apart from the fan mounting hole 1336 toward the outer edge of the seating surface 1331. The flow guide 32 is fixed to the accommodation portion 133 by a coupling member passing through the flow guide coupling hole 1331*a*.

In addition, a flow guide hook 1339 and a filter hook 1338 are disposed to be spaced apart from each other in the front and rear direction on the coupling surface 1335 constituting the accommodation portion 133. The flow guide hook 1339 is disposed closer to the seating surface 1331 than the filter hook 1338.

In addition, a gripping groove 1337 is defined at a side end of the rear surface of the rear body 13 corresponding to a rear side of the filter hook 1338. In detail, it may be described that the gripping groove 1337 is defined at a point at which the fusion portion 132 and the coupling surface 1335 meet each other.

Figure 8:
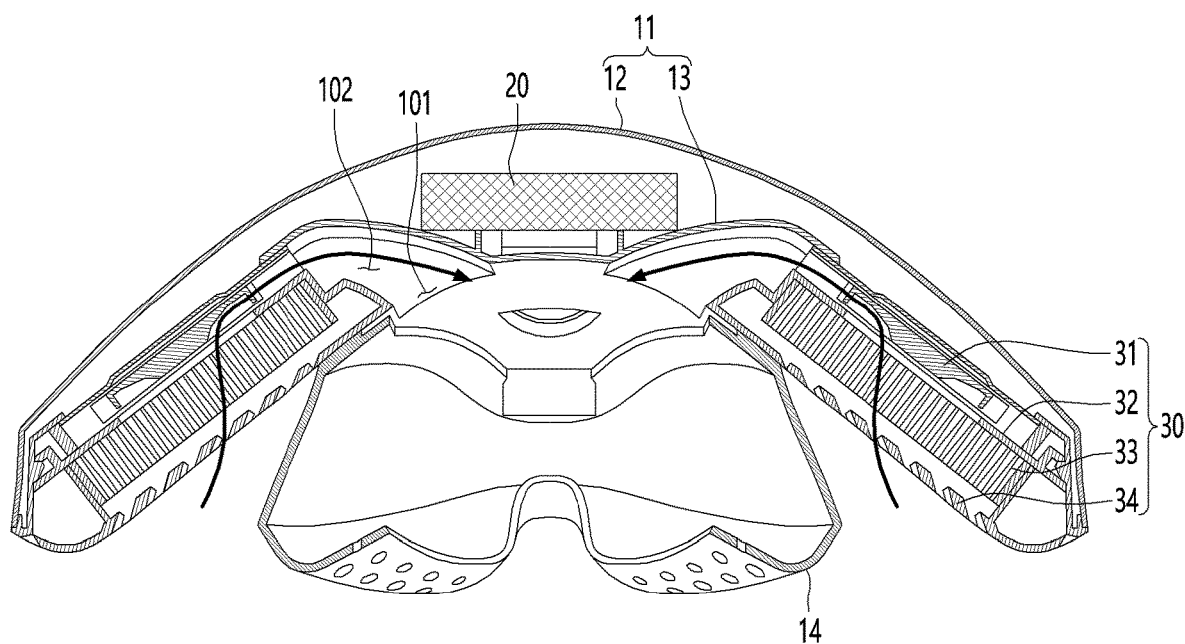
FIG. 8 is a transverse cross-sectional view of the mask apparatus according to an embodiment.
Figure 9:
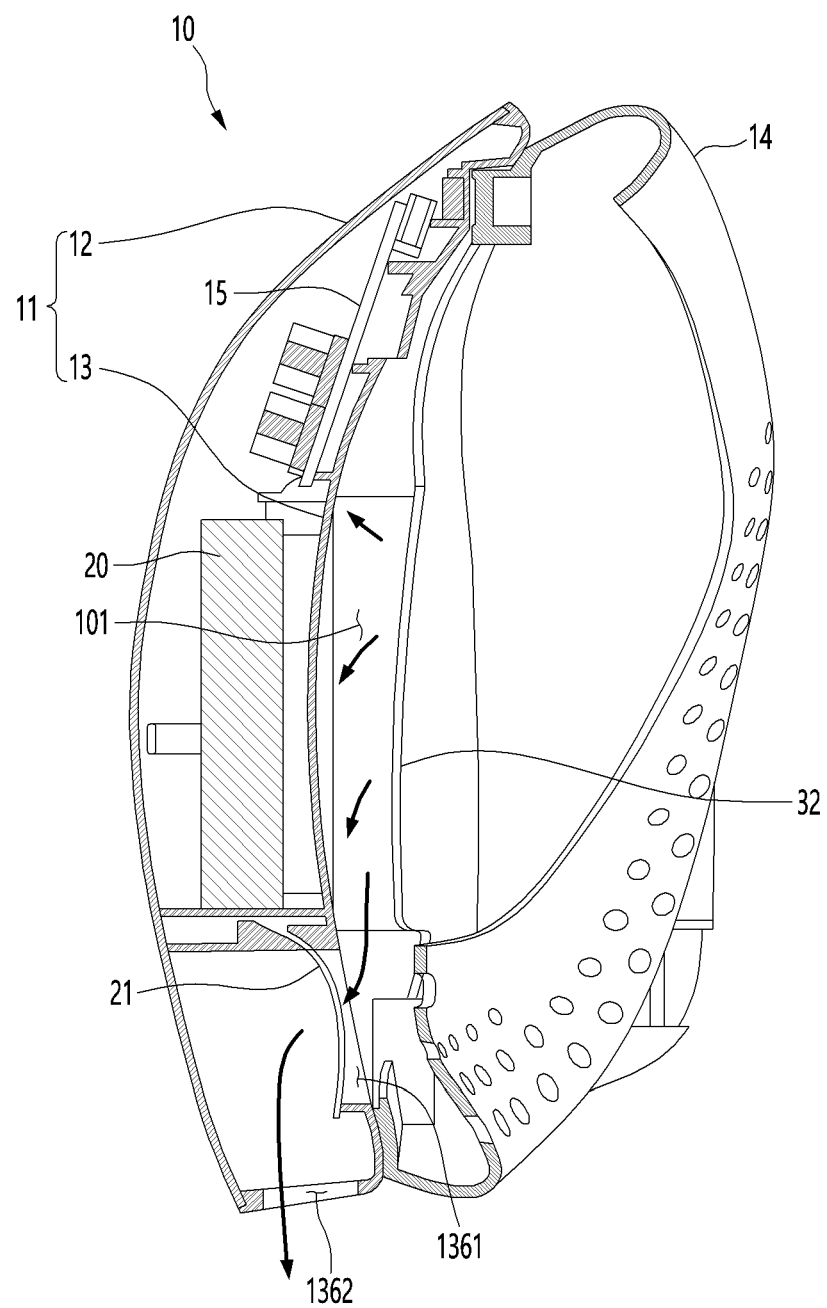
FIG. 9 is a longitudinal cross-sectional view of the mask apparatus.

FIG. 8 is a transverse cross-sectional view of the mask apparatus according to an embodiment, and FIG. 9 is a longitudinal cross-sectional view of the mask apparatus.

Referring to FIGS. 8 and 9, when the user operates the fan module 31 by pressing the power button, external air is introduced into the mask apparatus 10 through the suction grills 343 (or suction holes) disposed at the left and right sides of the rear surface of the mask apparatus 10.

The external air introduced through the suction grill 343 is purified while passing through the filter 33. Then, the air passing through the filter 33 is suctioned in an axial direction of the fan module 31 and then discharged in a radial direction.

As illustrated in FIG. 8, a front surface of the fan module 31 is seated on the seating surface 1331, and a rear surface of the fan module 31 is opened. In addition, the opened rear surface of the fan module 31 is shielded by the flow guide 32, and a communication hole serving as an suction hole of the fan module 31 is defined in the flow guide 32. The air passing through the filter 33 is introduced into the fan through the communication hole.

Also, an air duct 102 is defined between a side surface of the flow guide 32 and the air guide surface 1334. In addition, an inlet of the air duct 102 communicates with an outlet (or discharge hole) of the fan module 31, and the outlet of the air duct 102 communicates with the discharge hole 101.

In addition, the discharge hole 101 is defined in the breathing space defined by the rear surface of the face guard 14 and the rear body 13. Therefore, the external air suctioned by the fan module 31 is discharged to the breathing space, so that the user inhales.

In addition, the air guide surface 1334 is provided to be smoothly rounded from the outlet of the fan module 31 toward the discharge hole 101, so that the air discharged in the radial direction of the fan module 31 is not sharply changed in flow direction while flowing toward the discharge hole 101.

In detail, in the case of the centrifugal fan, the discharge of the air in the axial suction and radial discharge are due to a shape of a cone or truncated cone hub. That is, the air suctioned in the axial direction of the centrifugal fan is smoothly changed in direction to 90 degrees along the round surface of the hub.

Here, since the rounded direction of the hub constituting the fan module 31 and the rounded direction of the air guide surface 1334 are the same, the air suctioned into the fan module 31 smoothly flows in only one direction.

If the suction grill 343 is provided on the front body 12, the suction hole of the fan module 31 faces the front body 12, and as a result, the rounded direction of the hub constituting the fan module is opposite to the rounded direction of the air guide surface 1334. As a result, the air discharged from the fan module 31 collides with the beginning of the air guide surface 1334 corresponding to the suction hole of the air duct 102 to generate flow resistance and flow noise.

That is, the air suctioned in the axial direction of the fan module 31 substantially generates an S-shaped flow, resulting in a greater flow loss than the structure, in which the C-shaped or n-shaped flow is generated, according to an embodiment.

When the user exhales, the air discharged through the user's mouth and nose is collected in the breathing space. A minute portion of the air collected in the breathing space is introduced into the pressure sensor mounting portion 130 through the through-hole 1301.

In addition, most of the air collected in the breathing space descends and is discharged to the outside through the front exhaust port 1361 and the bottom exhaust port 1362. Here, as the exhaust valve 20 is bent forward by the pressure of air generated when the user exhales, the front exhaust port 1361 is opened. In addition, when the user inhales, the pressure inside the breathing space is lower than atmospheric pressure, and the exhaust valve 20 returns to its original position to shield the front exhaust port 1361.

Figure 10:
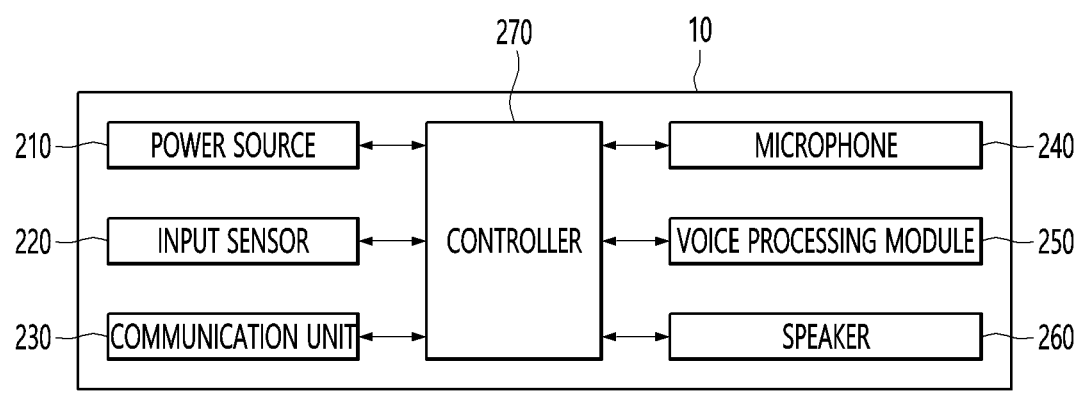
FIG. 10 is a block diagram illustrating constituents of the mask apparatus according to an embodiment.

FIG. 10 is a block diagram illustrating constituents of the mask apparatus according to an embodiment.

Referring to FIG. 10, the mask apparatus 10 may include some or all of a power source 210, a pressure sensor 220, a communication portion 230, a microphone 240, a voice processing module 250, a speaker 260, and a controller 270.

The power source 210 functions to turn on or off power of the mask apparatus 10. When the power source 210 is turned on, driving of the mask apparatus 10 may start, and electronic components provided in the mask apparatus 10 may operate.

The power source 210 may be configured as a button outside or inside the mask apparatus 10. The power source 210 may be implemented in a physical key or a touch key manner on the outside of the mask apparatus 10. Thus, the user may manipulate the power source 210 while wearing the mask apparatus 10.

In addition, the power source 210 may be turned on or off by voice recognition. For example, preset voice information may be stored in the mask apparatus 10, and the power source 210 may be turned on or off by receiving a voice command from the user.

In addition, the power source 210 may be manipulated by an external device communicatively connected thereto. For example, the mask apparatus 10 may receive a control command from the external device (e.g., a mobile terminal, a computer, a wearable device, etc.), and the power of the power source 210 may be turned on or off according to the control command.

The pressure sensor 220 functions to sense or measure an internal pressure of the mask apparatus 10. The pressure sensor 220 may be disposed inside the pressure sensor mounting portion 130.

Here, the internal pressure of the mask apparatus 10 may mean a pressure in a breathing space defined by the user's face and the face guard 14.

The pressure sensor 220 may be a pressure sensor that measures a pressure or air pressure in a sealed space by using a flow rate or wind strength of air flowing into the mask apparatus 10. Alternatively, the pressure sensor 220 may be a differential pressure sensor that measures a pressure change in a sealed space. Since the pressure sensor 220 is the well-known technology, a detailed description thereof will be omitted.

Information measured by the pressure sensor 220 may be provided to the controller 270 to be described later.

The communication portion 230 is configured to communicatively connect the mask apparatus 10 to the external device. The external device may include various electronic devices such as a mobile terminal, a computer, and a wearable device.

The communication portion 230 may be communicatively connected to the external device in a wireless communication manner. For example, the communication portion 230 may use various short-distance communication methods such as Bluetooth communication and Wi-Fi communication. Also, the communication portion 230 may be communicatively connected to the external device through long-distance communication.

The microphone 240 is configured to receive an external sound or a user's voice. The microphone 240 may be disposed in an inner space of the mask apparatus 10 to receive the user's voice clearly.

For example, the microphone 240 may be disposed at one side of the breathing space of the mask apparatus 10. The microphone 240 may be disposed inside the pressure sensor mounting portion 130 and may be disposed adjacent to the pressure sensor 220.

The voice processing module 250 converts a voice signal input from the microphone 240 into an electrical signal to provide the converted electrical signal to the speaker 260 to be described later.

The voice processing module 250 may give a predetermined frequency characteristic to the input voice signal to compensate an input signal level of the voice signal.

For example, during the user's utterance, a voice signal input through the microphone 240 may be distorted by various factors and output as it is. In this case, the output voice signal may have a limitation of showing characteristics different from the actual voice.

To solve this limitation, the voice processing module 250 may apply an equalizer to the input voice signal to correct a portion different from the actual original sound for each frequency.

Also, the voice processing module 250 may restrict an output of the input signal having an input signal level equal to or higher than a predetermined level among the voice signals input from the microphone 240.

For example, a howling phenomenon may occur because the microphone 240 and the speaker 260 are close to each other due to the structural characteristics of the mask. In this case, the voice signal output from the speaker 260 may be input to the microphone 240, amplified by the amplifier, and output to the speaker.

Thus, to prevent this limitation, the voice processing module 250 may apply a compressor that restricts the output by setting a critical value so that the input signal level of the input voice signal does not increase above a certain level.

Also, the voice processing module 250 may block an output of the input signal having an input signal level less than a predetermined level among the voice signals input from the microphone 240.

For example, the fan noise, which is generated while the fan of the mask apparatus 10 operates, and the user's breathing sound may be input to the microphone 240 and then amplified by the amplifier and output to the speaker 260.

Thus, to prevent the limitation, the voice processing module 250 may apply a noise gate that blocks an output of the input signal of which an input signal level is less than a predetermined level among the input voice signals.

The speaker 260 functions to receive a mechanical signal converted by the voice processing module 250 to output a sound to the outside. The speaker 260 may convert the provided mechanical signal into a voice signal to amplify the voice signal, thereby outputting the amplified voice signal to the outside.

The speaker 260 may be installed on a front surface of the mask body 10. In addition, the sound output from the speaker 260 may be transmitted to the outside through a speaker hole (not shown) defined in the mask body cover 20.

The controller 270 functions to control and monitor the overall function of the mask apparatus 10. The controller 270 may control the power source 210, the pressure sensor 220, the communication portion 230, the microphone 240, the voice processing module 250, and the speaker 260.

Particularly, the controller 270 may measure an internal pressure of the mask using the pressure sensor 220 and compare the measured internal pressure to a reference pressure value to control the voice output of the speaker 260.

In addition, the controller 270 may determine the user's breathing state (breathing characteristics) using the pressure sensor 220 and control the voice output of the speaker 260 based on the breathing state.

Figure 11:
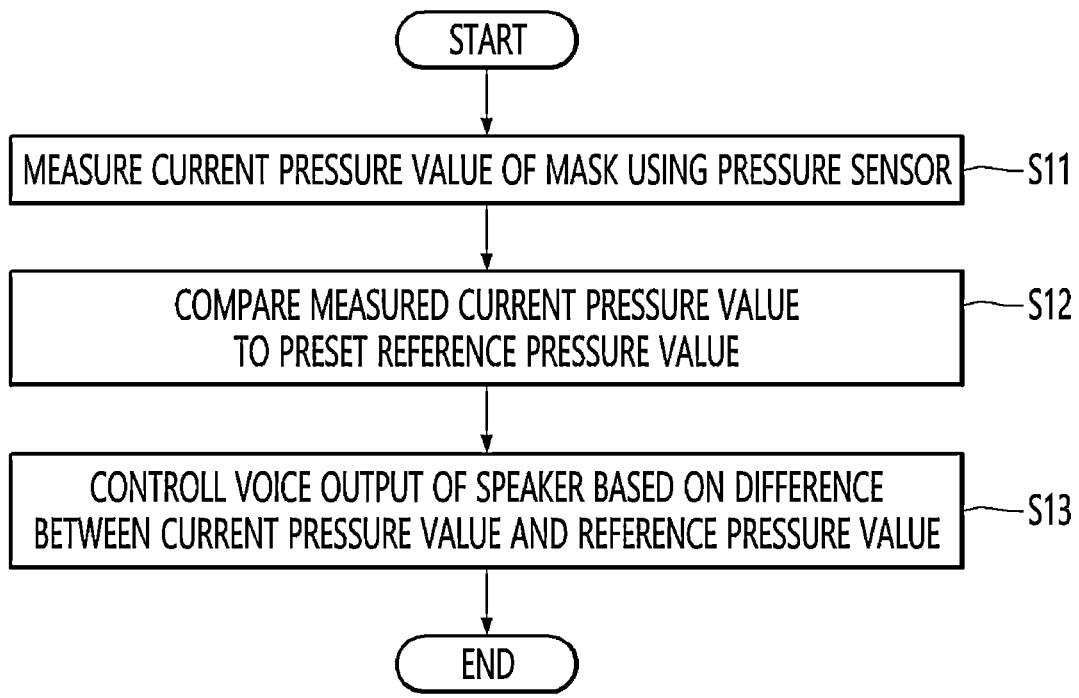
FIG. 11 is a schematic flowchart illustrating a method for controlling a mask apparatus according to an embodiment.

FIG. 11 is a schematic flowchart illustrating a method for controlling a mask apparatus according to an embodiment.

Referring to FIG. 11, a mask apparatus 10 measures a current pressure value of a mask using a pressure sensor 220.

Here, the current pressure value of the mask may mean a pressure of the breathing space defined by the user's face and the face guard 14.

When the power of the mask apparatus 10 is turned on, or the power of the speaker 260 is turned on, the mask apparatus 10 may drive the pressure sensor 220 to measure the internal pressure of the mask (S11).

The mask apparatus 10 compares the measured current pressure value to a preset reference pressure value and controls the voice output of the speaker 260 based on a difference between the current pressure value and the reference pressure value.

Here, the reference input value may be an intermediate value between a maximum pressure value and a minimum pressure value among pressure values measured for a predetermined time by the pressure sensor 220.

When the measured current pressure value is less than the reference pressure value, the mask apparatus 10 may determine that the user's breathing state is an inhaling state to deactivate the voice output function of the speaker 260 or mute the sound.

In addition, when the measured current pressure value is less than the reference pressure value, the mask apparatus 10 may determine that the user's breathing state is an exhaling state to activate the voice output function of the speaker 260 or release the mute state (S12, S13).

Figure 12:
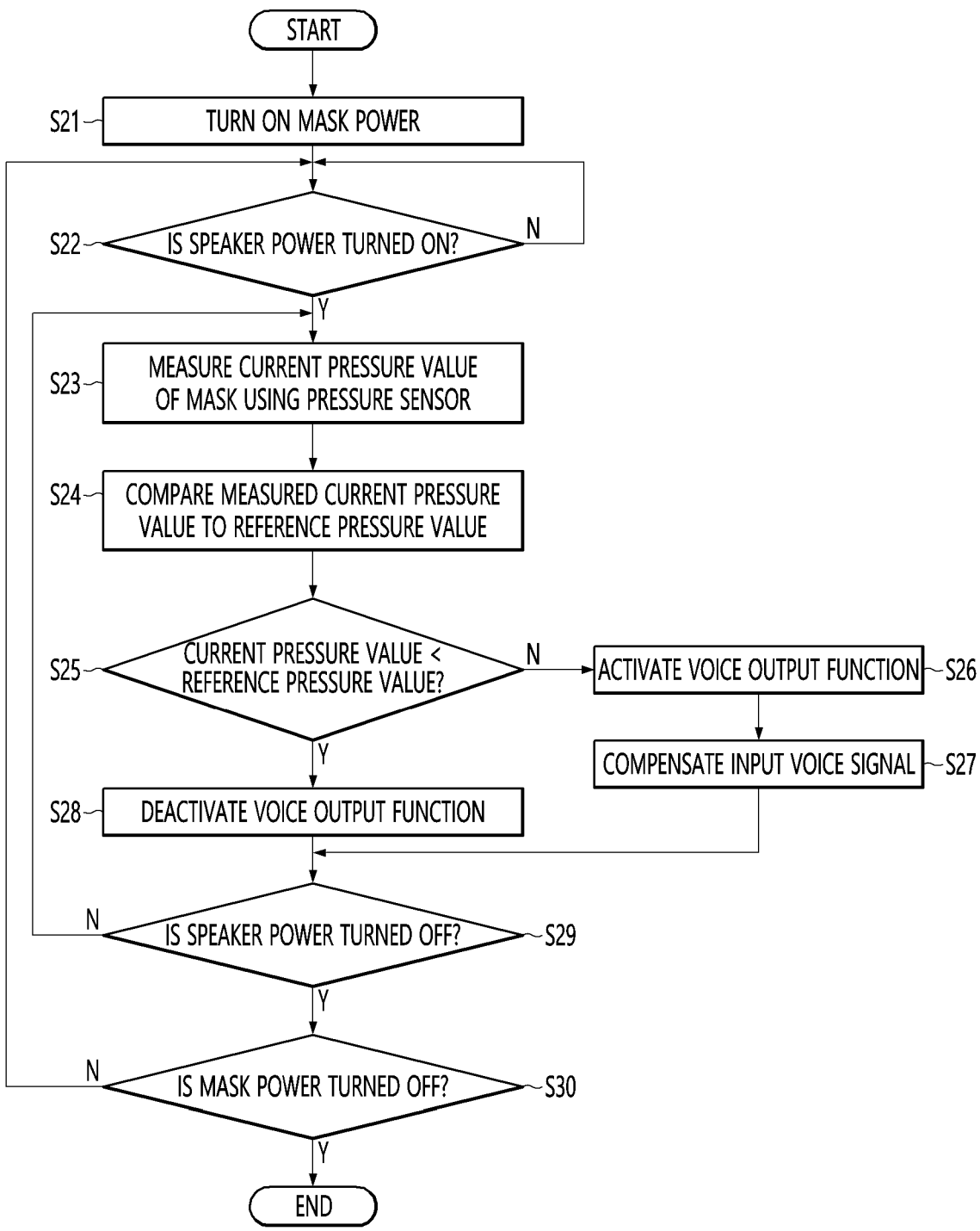
FIG. 12 is a detailed flowchart illustrating the method for controlling a mask apparatus according to an embodiment.
Figure 13:
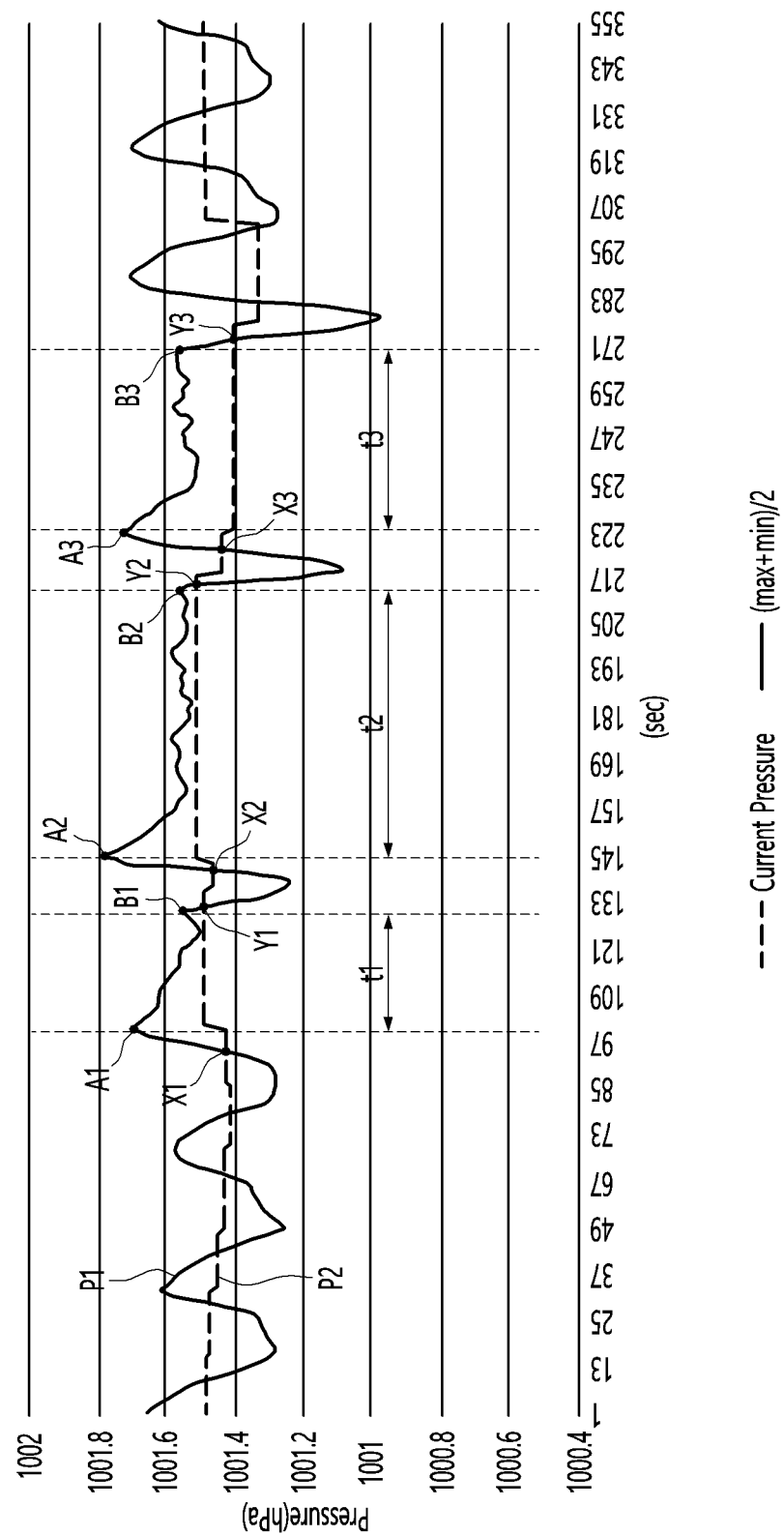
FIG. 13 is a graph showing a change in pressure of a mask according to user's breathing and utterance according to an embodiment.

FIG. 12 is a detailed flowchart illustrating the method for controlling the mask apparatus according to an embodiment, and FIG. 13 is a graph showing a change in pressure of the mask according to user's breathing and utterance according to an embodiment.

First, referring to FIG. 12, when the power of the mask apparatus 10 is turned on, it is determined whether the power of the speaker 260 is turned on.

Here, when the power of the speaker 260 is turned on, it may mean that the power of the speaker 260 and the power of the microphone 240 are turned on together.

Also, even if the power of the speaker 260 is turned on, the output function (amplification function) of the speaker 260 is not unconditionally performed. For example, when the voice output function is deactivated even when the power of the speaker 260 is turned on, the output function of the speaker 260 may not be performed.

That is, the output function of the speaker 260 may be performed only when the voice output function is activated while the power of the speaker 260 is turned on.

The power of the mask apparatus 10 may be turned on by pressing the power button (or a manipulation portion) provided at one side of the mask apparatus 10. In this case, when the power button is pressed for a predetermined time or more, the power of the mask apparatus 10 may be turned on.

When the power button is selected again in the state in which the mask apparatus 10 is powered on, the power of the speaker 260 may be turned on. Here, if the power button is selected again in the state in which the power of the speaker 260 is on, the power of the speaker 260 may be turned off.

In addition, when the power button is pressed for a predetermined time or more in the state in which the power of the mask apparatus 10 is turned on, the power of the mask apparatus 10 may be turned off.

In addition, the power of the mask apparatus 10 and the power of the speaker 260 may be manipulated by an external device communicatively connected thereto. For example, the mask apparatus 10 receives a control command from the external device (e.g., a mobile terminal, a computer, a wearable device, etc.), and the power of the mask apparatus 10 or the power of the speaker 260 may be turned on or off according to the control command.

According to this configuration, the user may operate the speaker 260 only when talking while wearing the mask apparatus 10. In addition, both the power of the mask apparatus 10 and the power of the speaker 260 may be manipulated by a simple operation of the power button (S21 and S22).

When the power of the speaker 260 is turned on, the mask apparatus 10 measures the current pressure value of the mask using the pressure sensor 220.

Here, the current pressure value of the mask may mean a pressure of the breathing space defined by the user's face and the face guard 14.

In detail, when the user breathes while wearing the mask apparatus 10, the pressure in the breathing space may be changed according to the user's breathing state. When the user exhales, the pressure in the breathing space may increase, and when the user inhales, the pressure in the breathing space may decrease.

Using this principle, the pressure sensor 220 may measure the pressure of the breathing space and predict the user's breathing state (breathing characteristics) through the measured pressure value (S23).

The mask apparatus 10 compares the measured current pressure value to the reference pressure value to determine whether the current pressure value is less than the reference pressure value.

Here, the reason for comparing the current pressure value to the reference pressure value is for determining whether the user's breathing state, i.e., whether the user is in the exhaling state, in which the user exhales, or an inhaling state, in which the user inhales.

Specifically, referring to FIG. 13, a horizontal axis of the graph indicates the passage of time, and a vertical axis of the graph indicates an amount of change in pressure. In FIG. 13, a solid line graph P1 indicates a current pressure value measured by the pressure sensor 220, a dotted line graph P2 indicates a reference pressure value, and t1, t2, and t3 indicate utterance sections in which user actually utters.

As illustrated in FIG. 13, when the user breathes while wearing the mask apparatus 10, the pressure sensor 220 may acquire pressure data for the breathing space.

The pressure data may include a pressure value measured in real time, and thus, a maximum pressure value and a minimum pressure value in a single breathing cycle (time taken for one inhalation and one exhalation) may be checked during one breathing.

In detail, when the user inhales air (inhalation), the air in the breathing space may be introduced into the user's nose so that the pressure in the breathing space may gradually decrease, and when the user exhales air (exhalation), the air may be introduced into the breathing space so that the pressure of the breathing space may gradually increase.

It may be predicted that a point at which the pressure of the breathing space is the highest is a point at which the exhalation is finished, and a point at which the pressure of the breathing space is the lowest is a point at which the inhalation is finished. Thus, the inhalation may starts for a predetermined time from the point at which the exhalation is finished, and the exhalation may starts for a predetermined time from the point at which the inhalation is finished.

However, the user does not utter while inhaling. That is, the user starts to utter only in the exhaling state and does not utter in the inhaling state. Therefore, in the present disclosure, due to this principle, the voice output of the speaker 260 is activated when the user's breathing state is the exhaling state (a state in which the utterance is possible), and the voice output of the speaker 260 is deactivated in the inhaling state (a state in which the utterance is impossible).

According to an embodiment, if the current pressure value P1 is greater than the reference pressure value P2, it may be determined as the exhaling state (the state in which the utterance is possible), and if the current pressure value P1 is less than the reference pressure value P2, it may be determined as the inhaling state (the state in which the utterance is impossible).

In this embodiment, the reference pressure value P2 may be an intermediate value between a maximum pressure value and a minimum pressure value among pressure values measured in once breathing cycle.

It may be seen that the user's utterance sections t1, t2, and t3 are substantially defined in the exhaling state in which the current pressure value P1 is greater than the reference pressure value P2 (S24 and S25).

The mask apparatus 10 activates the voice output function when the current pressure value is greater than the reference pressure value.

Specifically, when the current pressure value P1 is greater than the reference pressure value P2, it means that the user is in the exhaling state and in the state in which the utterance is possible. Thus, the voice output of the speaker 260 may be activated in advance at first time point X1, X2, X3 before user's utterance start time point A1, A2, A3.

In this case, the activation of the voice output of the speaker 260 may include a process of amplifying an input signal level of the voice signal input from the microphone 240 or a process of releasing the mute state of the microphone 240. Thus, when the user speaks while wearing the mask, the voice may be amplified and output to the outside (S26).

Also, the mask apparatus 10 may compensate the voice signal input from the microphone 240.

Specifically, when the current pressure value is greater than the reference pressure value, the mask apparatus 10 may activate the voice output of the speaker 260 to compensate the voice signal input from the microphone 240.

For example, the mask apparatus 10 may perform an equalizer that compensates the input signal level of the voice signal by giving a predetermined frequency characteristic to the voice signal input from the microphone 240.

Figure 14:
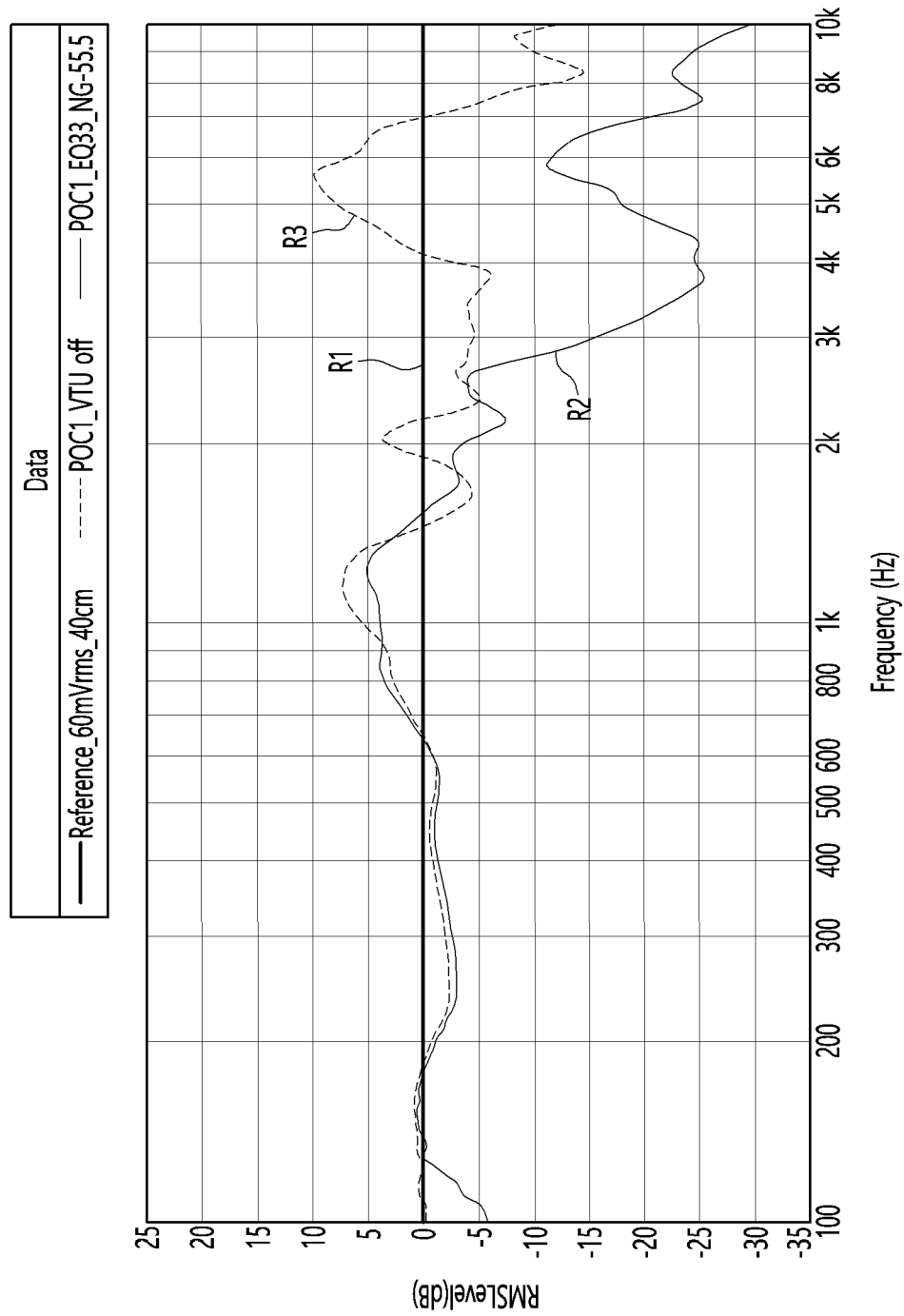
FIG. 14 is a graph showing frequency characteristics due to an application of an equalizer according to an embodiment.

FIG. 14 is a graph showing frequency characteristics due to the application of the equalizer according to an embodiment.

Referring to FIG. 14, a horizontal axis of the graph indicates a frequency magnitude of the speaker, and a vertical axis of the graph indicates a root mean square (RSM) of the speaker.

In FIG. 14, a thick solid line graph indicates a reference signal R1 directly output from an artificial mouth, and a dotted line graph indicates an output signal R2 when the voice amplification function is turned off while wearing the mask on the artificial mouth. In addition, a solid line graph indicates an output signal R3 when the voice amplification function (equalizer) is turned on while wearing the mask on the artificial mouth.

As illustrated in FIG. 14, when the output signal R2 having the voice amplification function (equalizer) turned off and the reference signal R1 are compared to each other, it is seen that attenuation in a band of about 3 kHz to about 4 kHz and a band of about 8 kHz to about 9 kHz is relatively high, and attenuation in a band of about 5 kHz to about 6 kHz is relatively low.

Therefore, in the present disclosure, to solve this limitation, the frequency characteristics may be improved by maximally amplifying the band of about 3 kHz to about 4 kHz and the band of about 8 kHz to about 9 kHz and relatively less amplifying the band of about 5 kHz to about 6 kHz in the equalizer setting.

As described above, the mask apparatus 10 may apply the equalizer to the input voice signal to correct a portion that is different from an actual original sound for each frequency.

Also, the mask apparatus 10 may restrict an output of an input signal having an input signal level equal to or higher than a predetermined level (a first level) among the voice signals input from the microphone 240.

Figure 15:
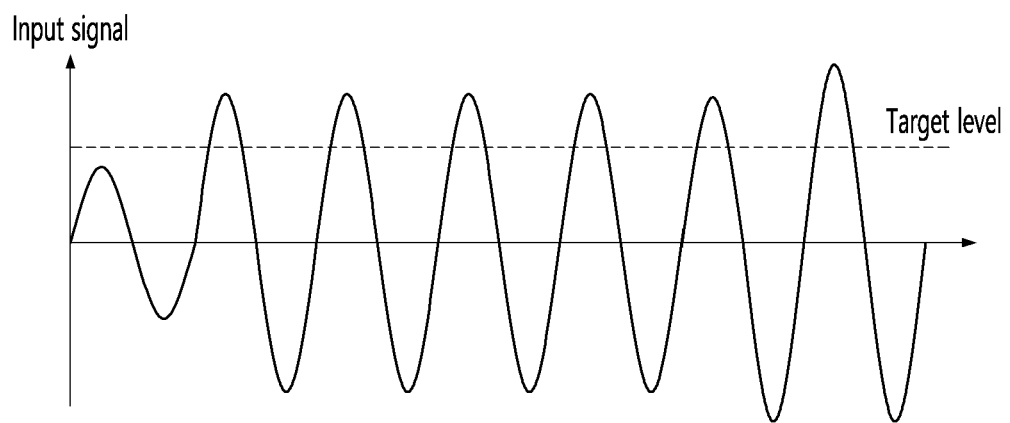
FIGS. 15(A) and (b) are graphs showing frequency characteristics due to an application of a compressor according to an embodiment.
Figure 15:
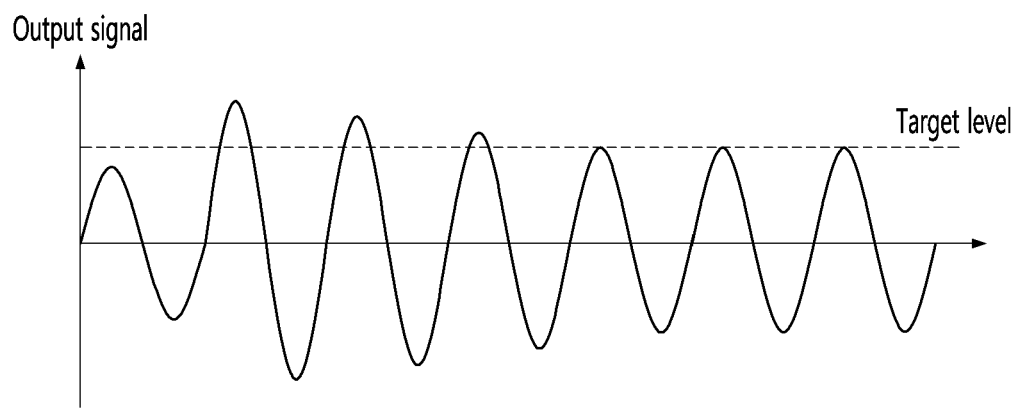

FIG. 15 is a graph showing frequency characteristics due to an application of a compressor according to an embodiment.

Referring to FIG. 15, (A) of FIG. 15 illustrates a frequency of a voice signal input from the microphone 240, and (B) of FIG. 15 illustrates a frequency of a voice signal output from the speaker 260. A horizontal axis of the graph indicates a passage of time, and a vertical axis of the graph indicates a magnitude of a frequency.

In the present disclosure, due to the structural characteristics of the mask, the microphone 240 and the speaker 260 are close to each other to cause a howling phenomenon. In this case, the voice signal output from the speaker 260 may be input to the microphone 240, amplified by the amplifier, and output to the speaker.

Thus, to solve this limitation, the mask apparatus 10 may apply a compressor that restricts an output by setting a critical value so that the input signal level of the input voice signal does not increases above a predetermined first level.

As a result, when the input signal level greater than the target level is received from among the input signal levels of the input voice signal, the output of the input signal level greater than the target level may be limited to the target level. Thus, there is an advantage in that a high sound generated during the howling phenomenon is suppressed by restricting an output of the high sound above a certain level.

Also, the mask apparatus 10 may block an output of an input signal having an input signal level less than a predetermined level (second level) among the voice signals input from the microphone 240.

Figure 16:
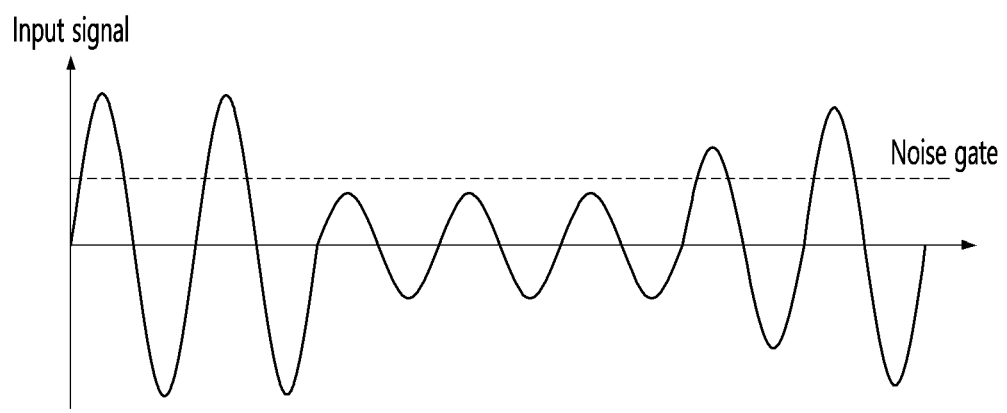
FIGS. 16(A) and (b) are graphs showing frequency characteristics due to an application of a noise gate according to an embodiment.
Figure 16:
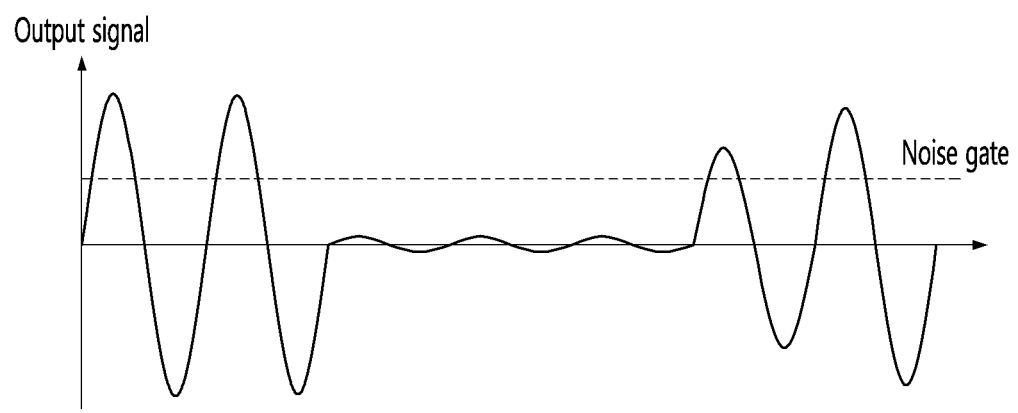

FIG. 16 is a graph showing frequency characteristics due to an application of a noise gate according to an embodiment.

Referring to FIG. 16, (A) of FIG. 16 illustrates a frequency of a voice signal input from the microphone 240, and (B) of FIG. 16 illustrates a frequency of a voice signal output from the speaker 260. A horizontal axis of the graph indicates a passage of time, and a vertical axis of the graph indicates a magnitude of a frequency.

In the present disclosure, the fan noise, which is generated while the fan of the mask apparatus 10 operates, and the user's breathing sound may be input to the microphone 240 and then amplified by the amplifier and output to the speaker 260.

Thus, to solve this limitation, the mask apparatus 10 may apply the noise gate that blocks an output of an input signal of which an input signal level is less than a predetermined second level among the input audio signals.

As a result, when the input signal level less than a target level is input from among the input signal levels of the input voice signal, the output of the input signal level less than the target level may be blocked or removed. Thus, there is an advantage in that noise such as the breathing sound and the fan noise is suppressed by determining that the input signal less than the certain level is noise to block the output (S27).

When the current pressure value is less than the reference pressure value, the mask apparatus 10 deactivates the voice output function.

Specifically, when the current pressure value P1 is less than the reference pressure value P2, it means that the user is in the inhaling state and in the state in which the utterance is impossible. Thus, the voice output of the speaker 260 may be deactivated at second time points Y1, Y2, and Y3 after user's utterance end time points B1, B2, and B3.

Here, the deactivation of the voice output of the speaker 260 may include a process of ignoring the input signal of the voice signal input from the microphone 240 or a process of muting a sound output from the microphone 240. Thus, the user may prevent the breathing sound, the fan noise, or the noise from being inputted to the microphone 240 and outputted to the speaker 260 after the utterance is ended (S28).

Thereafter, the mask apparatus 10 determines whether the power of the speaker 260 is turned off, and if the power of the speaker 260 is not turned off, the process proceeds to operation S23 so as to measure the current pressure value of the mask again (S29).

If the power of the speaker 260 is turned off, the mask apparatus 10 determines whether the mask power is off, and if the mask power is off, an algorithm is ended, and if the mask power is not off, the process proceeds to operation S22 to determine again whether the power of the speaker 260 is turned on (S30).

Another embodiment of the present disclosure is proposed.

In a method for controlling a mask apparatus according to another embodiment, a current pressure value of a mask may be measured using a pressure sensor 220, a user's breathing state may be determined based on a difference between the measured current pressure value and a preset reference pressure value, and a voice output of the speaker 260 may be controlled according to the determined breathing state.

Here, if the current pressure value is less than the reference pressure value, it is determined as the inhaling state to restrict or deactivate the voice output of the speaker 260.

On the other hand, if the current pressure value is greater than the reference pressure value, it is determined as the exhaling state to allow and activate the voice output of the speaker 260.

According to the method for controlling the mask according to an embodiment as described above, the following effects are obtained.

First, since the speaker's voice output (voice amplification) function is turned on/off according to the user's breathing characteristics, the mask touch may be reduced, which is convenient, and the sanitary condition of the mask may be improved.

Second, since the voice output function is activated when the user is in the state in which the utterance is possible, and the voice output function is deactivated when the user is in the state in which the utterance is impossible, the noise generation may be minimized, and the voice may be clearly output.

In detail, the user's breathing state may be determined using the pressure sensor provided in the mask, the voice output function may be deactivated in the inhaling state, and the voice output function may be activated in the exhaling state.

Therefore, there may be the advantage in that the voice amplification function operates in the timely manner when the user utters, and thus, the voice may be loudly and clearly output. In addition, since the output of the breathing sound or the fan noise is prevented during the non-utterance, there may be the advantage in that the effective conversation is achieved.

Third, since it is possible to compensate the input signal level of the voice signal by giving the predetermined frequency characteristic to the voice signal input to the microphone, there may be the advantage that the voice is clearly output by correcting the portion that is different from the actual original sound for each frequency.

Fourth, there may be the advantage in that the noise due to the howling phenomenon is prevented from occurring by restricting the output of the input signal having the input signal level equal to or higher than the certain level among the voice signals input to the microphone.

Fifth, there may be the advantage in that the noise such as the breathing sound and the fan noise is prevented from being output to the speaker by blocking the output of the input signal of which the input signal level is less than the certain level among the voice signals input to the microphone.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A mask apparatus comprising:
   a mask body in which a microphone and a speaker are installed;
   a face guard coupled to a rear surface of the mask body so as to be in close contact with a user's face and having a breathing space therein;
   a pressure sensor installed in the mask body to measure a pressure of the breathing space; and
   a controller configured to compare a current pressure value measured by the pressure sensor to a reference pressure value and control a voice output of the speaker based on a difference between the current pressure value and the reference pressure value,
   wherein the reference pressure value is an intermediate value between a maximum pressure value and a minimum pressure value among pressure values measured for a predetermined time by the pressure sensor.

2. The mask apparatus according to claim 1, wherein the controller, when controlling the voice output of the speaker, is configured to adjust an input signal level of a voice signal input from the microphone or mute the voice signal input from the microphone.

3. The mask apparatus according to claim 1, wherein, when the measured current pressure value is less than the reference pressure value, the controller is configured to deactivate a voice output function of the speaker or mute a voice.

4. The mask apparatus according to claim 1, wherein, when the measured current pressure value is greater than the reference pressure value, the controller is configured to activate a voice output function of the speaker or release a mute state.

5. The mask apparatus according to claim 1, wherein the controller is further configured to convert a voice signal input from the microphone into an electrical signal and to provide the converted electrical signal into the speaker.

6. The mask apparatus according to claim 5, wherein, when the measured current pressure value is greater than the reference pressure value, the controller is configured to give a predetermined frequency characteristic with respect to the voice signal input from the microphone so as to compensate an input signal level of the voice signal.

7. The mask apparatus according to claim 5, wherein, when the measured current pressure value is greater than the reference pressure value, the controller is configured to restrict an output of an input signal having an input signal level greater than a first level among input signals input from the microphone.

8. The mask apparatus according to claim 5, wherein, when the measured current pressure value is greater than the reference pressure value, the controller is configured to block an output of an input signal having an input signal level less than a second level among voice signals input from the microphone.

9. The mask apparatus according to claim 1, further comprising a communication module provided to the mask body to communicate with an external device,
   wherein the speaker is controlled by the external device.

10. A method for controlling a mask apparatus comprising a microphone, a speaker, and a pressure sensor, the method comprising:
    measuring a current pressure value with respect to the mask apparatus by using the pressure sensor;
    comparing the measured current pressure value to a reference pressure value; and
    controlling a voice output of the speaker based on a difference between the current pressure value and the reference pressure value,
    wherein the reference pressure value is an intermediate value between a maximum pressure value and a minimum pressure value among input values measured for a predetermined time by the pressure sensor.

11. The method according to claim 10, wherein the controlling of the voice output of the speaker comprises:
    adjusting an input signal level of a voice signal input from the microphone; or
    performing mute processing on the voice signal input from the microphone.

12. The method according to claim 10, wherein, when the measured current pressure value is less than the reference pressure value, a voice output function of the speaker is deactivated, or a voice is muted.

13. The method according to claim 10, wherein, when the measured current pressure value is greater than the reference pressure value, a voice output function of the speaker is activated, or a mute state is released.

14. The method according to claim 13, wherein, when the measured current pressure value is greater than the reference pressure value, a predetermined frequency characteristic with respect to the voice signal input from the microphone is given to compensate an input signal level of the voice signal.

15. The method according to claim 13, wherein, when the measured current pressure value is greater than the reference pressure value, an output of an input signal having an input signal level greater than a first level among input signals input from the microphone is restricted.

16. The method according to claim 13, wherein, when the measured current pressure value is greater than the reference pressure value, an output of an input signal having an input signal level less than a second level among voice signals input from the microphone is blocked.

17. The method according to claim 10, further converting a voice signal input from the microphone into an electrical signal to provide the converted electrical signal into the speaker.

18. The method according to claim 10, further comprising:
    communicating with an external device through a communication module provided in the mask apparatus; and
    receiving control information from the external device to control power of the speaker.

* * * * *